United States Patent
Figley et al.

(10) Patent No.: US 12,029,847 B2
(45) Date of Patent: **\*Jul. 9, 2024**

(54) SYSTEMS FOR INHALATION OF THERAPEUTIC AND DIAGNOSTIC GAS AND METHODS OF USE THEREOF

(71) Applicant: BEYOND AIR LTD, Rehovot (IL)

(72) Inventors: Curtis Figley, Edmonton (CA); Einav Levi, Ness Ziona (IL); Atai Ophir, Rehovot (IL); Yossef Av-Gay, Vancouver (CA)

(73) Assignee: BEYOND AIR LTD, Rehovot (IL)

( * ) Notice: Subject to any disclaimer, the term of this patent is extended or adjusted under 35 U.S.C. 154(b) by 68 days.

This patent is subject to a terminal disclaimer.

(21) Appl. No.: 17/887,430

(22) Filed: Aug. 13, 2022

(65) Prior Publication Data

US 2023/0051940 A1    Feb. 16, 2023

Related U.S. Application Data

(63) Continuation of application No. 16/072,951, filed as application No. PCT/IB2017/000112 on Jan. 27, 2017, now Pat. No. 11,452,827.

(Continued)

(51) Int. Cl.
*A61M 16/00*     (2006.01)
*A61M 16/06*     (2006.01)
(Continued)

(52) U.S. Cl.
CPC .... *A61M 16/0003* (2014.02); *A61M 16/0051* (2013.01); *A61M 16/024* (2017.08);
(Continued)

(58) Field of Classification Search
CPC .......... A61M 16/0003; A61M 16/0051; A61M 16/06; A61M 16/08–085; A61M 16/0875; A61M 16/12–127; A61M 16/20–206; A61M 16/208–209; A61M 16/024; A61M 2016/102–1025; A61M 2016/1035; A61M 2206/11; A61M 2210/0618; A61M 2202/025; A61M 2202/0266–0283; A61M 16/0078; A61M 2202/0225; A61M 2016/003–0042; A61M 2202/02–0208; A61M 2205/3327
See application file for complete search history.

(56) References Cited

U.S. PATENT DOCUMENTS 5,483,955 A    1/1996   Morris
5,752,502 A    5/1998   King
(Continued)

FOREIGN PATENT DOCUMENTS

| JP | 2019509084 A | 4/2019 |
|---|---|---|
| WO | 2007012170 A1 | 2/2007 |
| WO | 2014159912 A1 | 10/2014 |

*Primary Examiner* — Elliot S Ruddie
(74) *Attorney, Agent, or Firm* — Elmore Patent Law Group, P.C.; Joseph C. Zucchero

(57) ABSTRACT

In one embodiment, the present invention provides a system to deliver at least one therapeutic gas to a spontaneously breathing patient, wherein the rate of delivery of the at least one therapeutic gas exceeds the patient's inspiratory flow rate, and the amount of the at least one therapeutic gas that is wasted is minimized or eliminated.

15 Claims, 26 Drawing Sheets

Related U.S. Application Data

(60) Provisional application No. 62/287,652, filed on Jan. 27, 2016.

(51) Int. Cl.
  *A61M 16/08* (2006.01)
  *A61M 16/10* (2006.01)
  *A61M 16/12* (2006.01)
  *A61M 16/20* (2006.01)

(52) U.S. Cl.
  CPC .......... *A61M 16/06* (2013.01); *A61M 16/085* (2014.02); *A61M 16/0875* (2013.01); *A61M 16/12* (2013.01); *A61M 16/208* (2013.01); *A61M 2016/0033* (2013.01); *A61M 2016/0036* (2013.01); *A61M 16/0078* (2013.01); *A61M 16/0833* (2014.02); *A61M 2016/1025* (2013.01); *A61M 2016/1035* (2013.01); *A61M 16/122* (2014.02); *A61M 2202/0208* (2013.01); *A61M 2202/0225* (2013.01); *A61M 2202/025* (2013.01); *A61M 2202/0275* (2013.01); *A61M 2205/3327* (2013.01); *A61M 2206/11* (2013.01); *A61M 2210/0618* (2013.01)

(56) References Cited

U.S. PATENT DOCUMENTS

| | | | |
|---|---|---|---|
| 6,192,884 B1 * | 2/2001 | Vann | A61M 16/00 |
| | | | 128/206.28 |
| 6,412,481 B1 | 7/2002 | Bienvenu et al. | |
| 2004/0060560 A1 * | 4/2004 | Stenzler | A61M 16/125 |
| | | | 128/207.12 |
| 2005/0145247 A1 | 7/2005 | Nashed et al. | |
| 2007/0062531 A1 | 3/2007 | Fisher et al. | |
| 2011/0277754 A1 | 11/2011 | McKinnon et al. | |
| 2013/0192595 A1 * | 8/2013 | Tolmie | A61M 16/024 |
| | | | 128/203.14 |
| 2013/0340756 A1 | 12/2013 | Slessarev et al. | |
| 2015/0034084 A1 | 2/2015 | Av-Gay et al. | |
| 2015/0272475 A1 * | 10/2015 | Buess | A61B 5/742 |
| | | | 600/531 |

\* cited by examiner

SYSTEMS FOR INHALATION OF THERAPEUTIC AND DIAGNOSTIC GAS AND METHODS OF USE THEREOF

RELATED APPLICATIONS

This application is a continuation of U.S. application Ser. No. 16/072,951, filed Jul. 26, 2018, which is a US National stage entry of International Application No. PCT/IB2017/000112, which designated the United States and was filed on Jan. 27, 2017, published in English, which claims the priority of U.S. Patent Application No. 62/287,652, filed Jan. 27, 2016; entitled "SYSTEM FOR NITRIC OXIDE INHALATION," which is incorporated herein by reference in its entirety for all purposes.

FIELD OF INVENTION

The present invention relates to a system to deliver at least one therapeutic gas to a spontaneously breathing patient, wherein the rate of delivery of the at least one therapeutic gas exceeds the patient's inspiratory flow rate, and the amount of the at least one therapeutic gas that is wasted is minimized or eliminated.

BACKGROUND

An inconsistent and inaccurate concentration of a therapeutic gas to a patient can reduce the effectiveness of the therapeutic gas administered to the patient.

SUMMARY

In one embodiment, the present invention provides a system configured to administer at least one therapeutic gas to a patient, comprising:
  a. at least one reservoir tube, having a proximal and a distal end, wherein the at least one reservoir tube has a volume larger than the tidal volume of the patient breath;
  b. at least one therapeutic gas inlet at the proximal end of the at least one reservoir tube, wherein a delivery tube is connected to the at least one therapeutic gas inlet and at least one therapeutic gas source; and
  c. a patient interface fluidly connected to the proximal end of the at least one reservoir tube via a check valve,
     wherein the patient interface is configured to form a gas-tight seal between the patient and the system,
     wherein the inhalation check valve is configured to be closed when the patient is exhaling,
     wherein the at least one therapeutic gas is introduced into the at least one reservoir tube at the proximal end through the at least one therapeutic gas inlet at a time average flow rate greater than the time average inhalation flow rate of the patient, and the at least one therapeutic gas flows along the at least one reservoir tube, from the proximal end to the distal end whilst the patient is exhaling,
     wherein the volume of the at least one therapeutic gas that is introduced into the at least one reservoir tube whilst the patient is exhaling, is greater than the patient's inhaled tidal volume, and
     wherein the inhalation check valve is configured to be open when the patient is inhaling, and
     wherein the inhalation check valve is configured to allow the at least one therapeutic gas to be administered to the patient.

In one embodiment, the system further comprises a second check valve, wherein the second check valve is configured to be closed whilst the patient is inhaling, and open whilst the patient is exhaling, and the system is configured to allow the second check valve to vent the gas exhaled by the patient.

In one embodiment, the system configured to administer at least one therapeutic gas to a patient is configured to minimize the effort required by the patient to either inhale, exhale, or both inhale and exhale.

In one embodiment, the at least one reservoir tube is further configured to minimize the effort required by the patient to either inhale, exhale, or both inhale and exhale.

In one embodiment, the system is configured to administer at least one therapeutic gas to a patient is further configured to monitor the flow of gas through the proximal end of the at least one reservoir tube.

In one embodiment, the system is configured to administer at least one therapeutic gas to a patient is further configured to monitor at least one parameter of the flow of gas through the proximal end of the at least one reservoir tube,
wherein the at least one parameter comprises: concentration, flow, contamination, or any combination thereof.

In one embodiment, the at least one reservoir tube further comprises a flow meter at the distal end.

In one embodiment, the at least one reservoir tube further comprises a flow meter responsive to the flow rate and flow direction in the reservoir, which for convenience may be located at the distal end of the reservoir.

In one embodiment, the system is configured to administer at least one therapeutic gas to a patient is further configured to monitor at least one parameter of the at least one therapeutic gas introduced into the system configured to administer at least one therapeutic gas to a patient, wherein the at least one parameter comprises: concentration, flow rate, flow volume, contamination level, or any combination thereof.

In one embodiment, the at least one reservoir tube further comprises a sampling port at the proximal end.

In one embodiment, the sampling port is configured to: deliver the gas to the patient, monitor the gas delivered to the patient, characterize the gas delivered to the patient, or any combination thereof. In one embodiment, the gas is characterized by content, contamination level, flow rate, flow volume, concentration, or any combination thereof.

In one embodiment, the system configured to administer at least one therapeutic gas to a patient is further configured to issue an alert if the monitored value of any one of the concentration the at least one therapeutic gas, or the corresponding flow rates deviate from a threshold value. As used herein, a threshold value may include either upper, lower, or in combination both upper and lower boundaries, above which, below which or outside of which respectively the monitored value is assessed to determine if a alert condition exists. As a non-limiting example, an upper and lower threshold for the allowable therapeutic level of the oxygen concentration might be used in a system to alert the operator if either a hyperoxic or hypoxic breathing mixture were being delivered.

In one embodiment, the system configured to administer at least one therapeutic gas to a patient is further configured to alter the flow rate, and/or the concentration of the at least one therapeutic gas if the monitored values of any one of the characteristics of the at least one therapeutic gas, or the flow rate deviates from at least one threshold value.

In one embodiment, the at least one therapeutic gas comprises: nitric oxide, helium, carbon dioxide, hyperoxic gas, hypoxic gas, a tracer gas, or combinations thereof. In one embodiment, the concentration of nitric oxide is 160 ppm in a mixture of oxygen and nitrogen. In one embodiment, the at least one therapeutic gas is nitric oxide. In one embodiment, the nitric oxide is at a concentration of 400 ppm to 0.5 ppm.

In some embodiments, the at least one therapeutic gas is a diagnostic gas.

In some embodiments, the at least one therapeutic gas is oxygen.

BRIEF DESCRIPTION OF THE DRAWINGS

FIG. 11 highlights an arrangement that uses a nasal mask and one inhalation check valve, wherein the patient is trained to breathe in through the nose and out through the mouth. FIG. 12 shows an embodiment where a face mask is used in conjunction with a double check valve "tee", wherein the tee incorporates the inhalation and exhalation check valves to direct the inhaled and exhaled gases. FIGS. 13 and 14 are similar to FIG. 12, but are alternately configured with a nose mask and a mouth piece so that the patient can optionally exhale through their mouth (per FIG. 13) and nose (per FIG. 14) to reduce expiratory effort.

DETAILED DESCRIPTION

Figure 1:
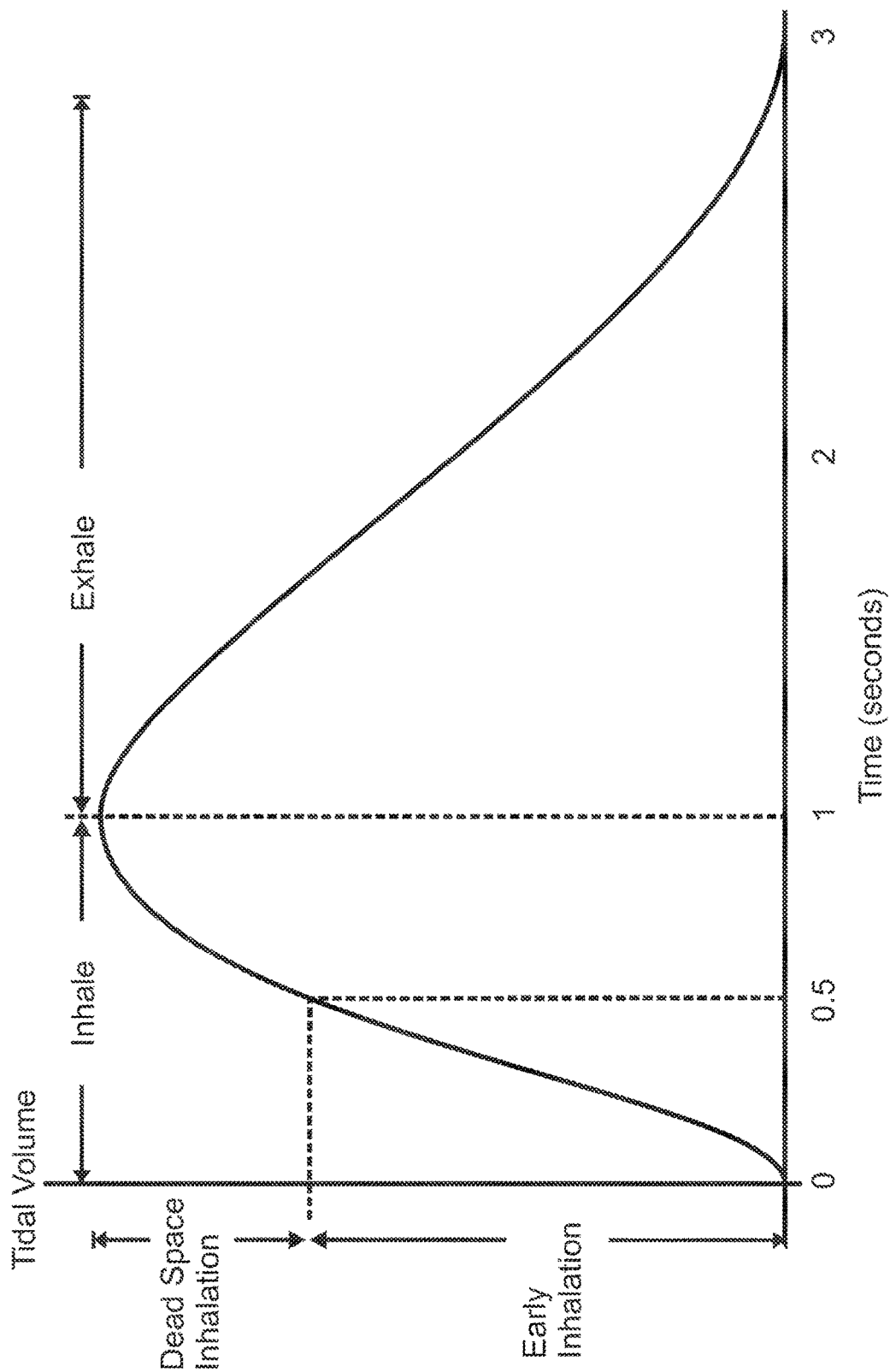
FIG. 1 shows a graph depicting the typical volume of air within the lungs during a typical inhalation cycle of a patient in need of the methods of treatment described herein.
Figure 2A:
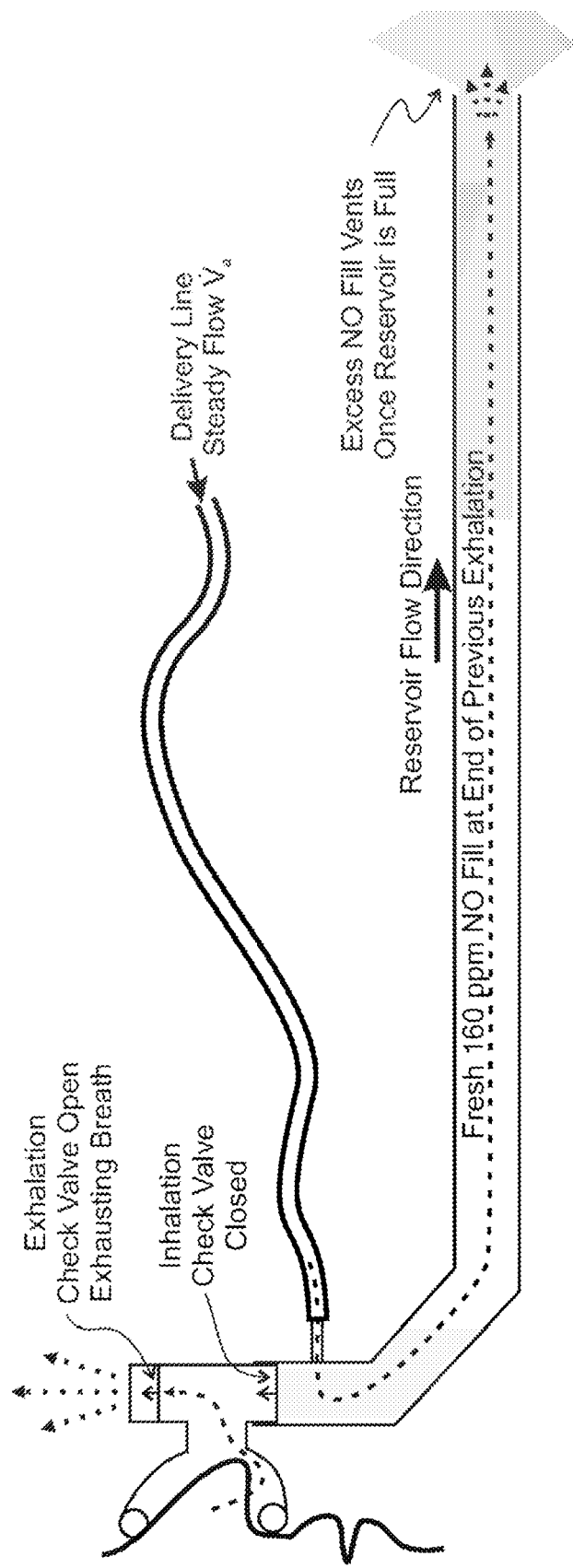
FIGS. 2(a) through 2(d) show the operation of a gas delivery system according to some embodiments of the present invention at key points through a patient's breathing cycle.
Figure 2B:
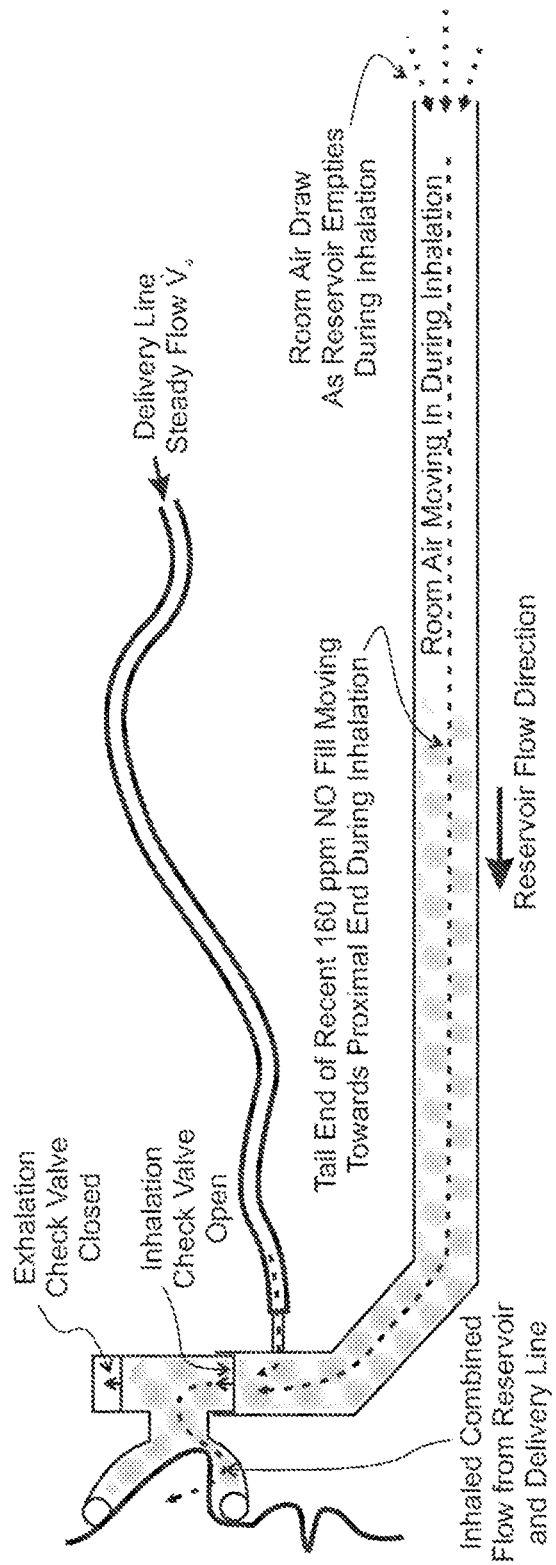
Figure 2C:
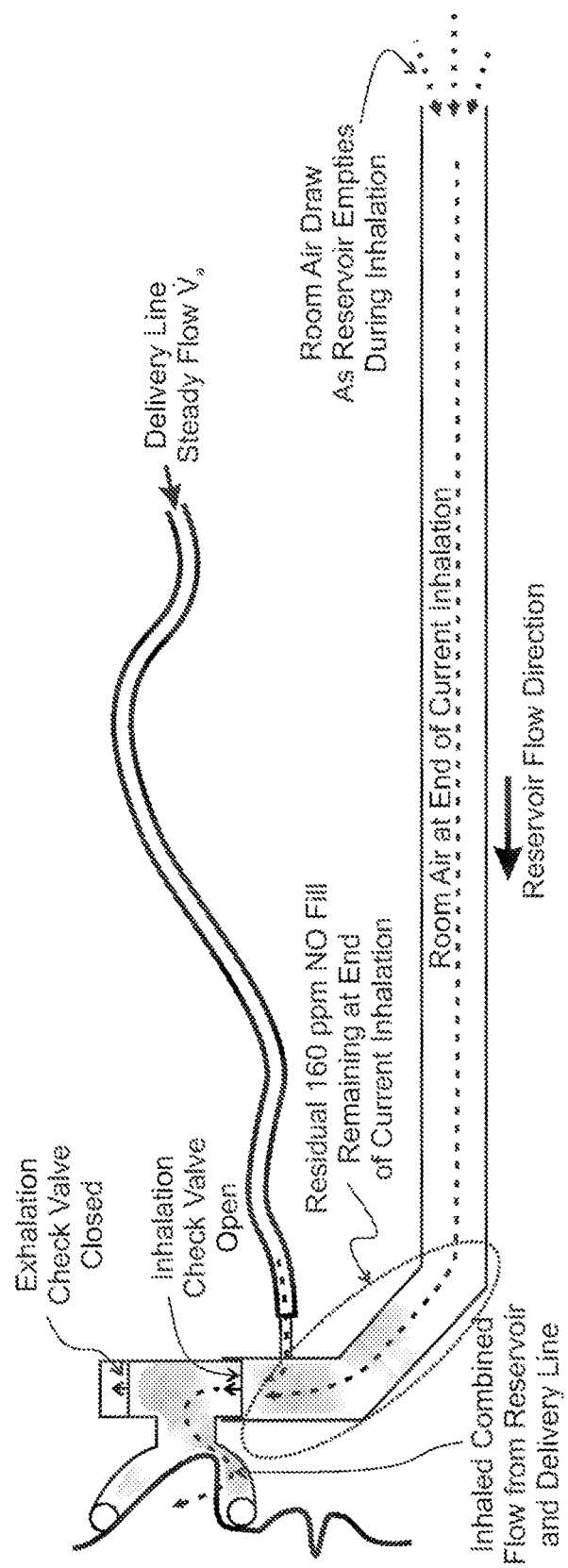
Figure 2D:
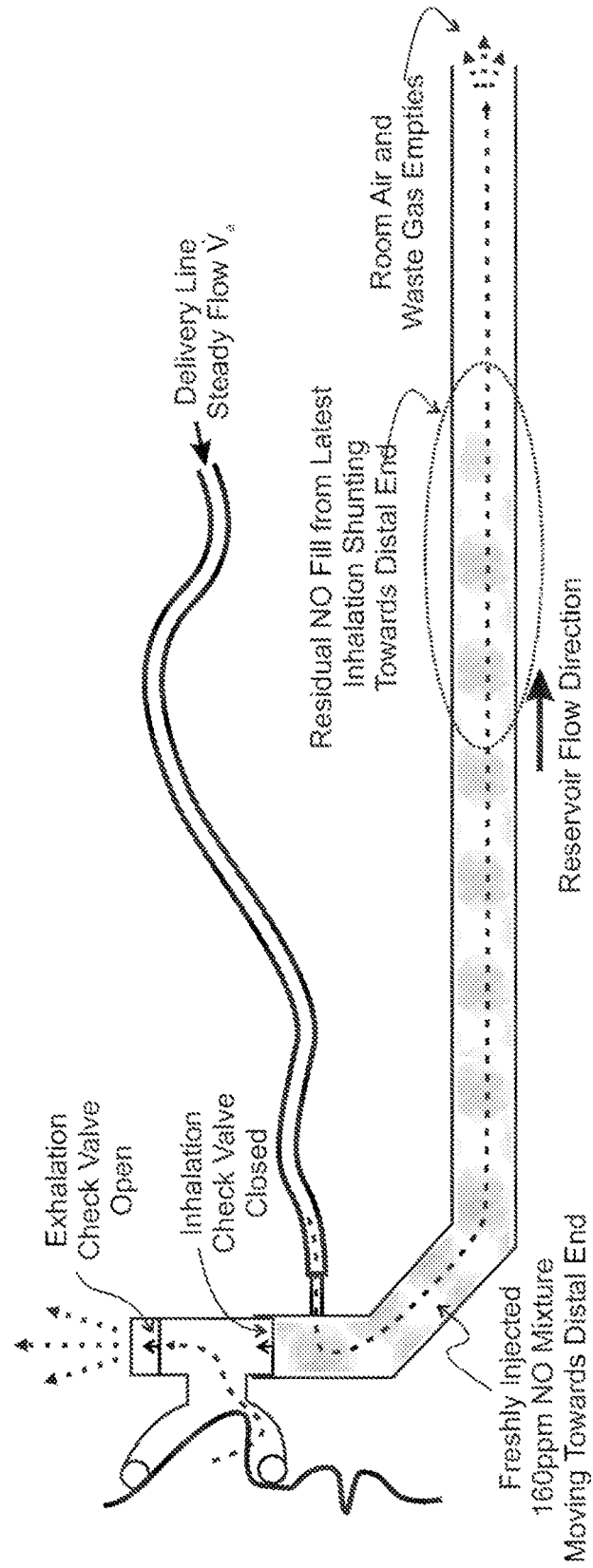

For clarity of disclosure, and not by way of limitation, the detailed description of the invention is divided into the following subsections that describe or illustrate certain features, embodiments or applications of the present invention.

In some embodiments, the present invention provides a system to deliver at least one therapeutic gas to a spontaneously breathing patient, wherein the average rate of delivery of the at least one therapeutic gas meets or exceeds the patient's average inspiratory flow rate. In some embodiments, the amount of the at least one therapeutic gas that is wasted is minimized or eliminated.

In some embodiments, the present invention provides a system configured to administer at least one therapeutic gas to a patient, comprising:
  a. at least one reservoir tube, having a proximal and a distal end, wherein the at least one reservoir tube has a volume larger than the tidal volume of the patient;
  b. at least one therapeutic gas inlet at the proximal end of the at least one reservoir tube, wherein a delivery tube is connected to the at least one therapeutic gas inlet and at least one therapeutic gas source; and
  c. a patient interface fluidly connected to the proximal end of the at least one reservoir tube via a check valve,
    wherein the patient interface is configured to form a gas-tight seal between the patient and the system,
    wherein the inhalation side of a check valve is configured to be closed when the patient is exhaling,
    wherein the at least one therapeutic gas is introduced into the at least one reservoir tube at the proximal end through the at least one therapeutic gas inlet at a time average flow rate greater than the time averaged inhalation flow rate of the patient (patient minute volume), and the at least one therapeutic gas flows along the at least one reservoir tube, from the proximal end to the distal end whilst the patient is exhaling,
    wherein the volume of the at least one therapeutic gas that is introduced into the at least one reservoir tube whilst the patient is exhaling, is greater than the patient's inhaled tidal volume, and
    wherein the inhalation check valve is configured to be open when the patient is inhaling, and
    wherein the inhalation check valve is configured to allow the at least one therapeutic gas to be administered to the patient.

In some embodiments, the at least one reservoir is configured to allow the therapeutic gas to flow between the proximal end and distal end and back as the steady injected flow alternately higher and then lower than the instant patient inspiratory flow. In some embodiments, the at least one reservoir is configured to move the therapeutic gas without substantial mixing in the longitudinal flow direction.

In some embodiments, the reservoir channel may typically have a cross section with a geometry, where the geometry can be, but is not limited to, round, elliptical, octagonal, square, rectangular, hexagonal, etc.

The following symbols, defined herein, are shown in the figures:
$\dot{V}_a$=total injected flow rate
$\dot{V}_x$=injected flow rate of a particular component gas stream, one of "n" possible components each designated by the subscript "x", such that $$\dot{V}_a = \sum_n \dot{V}_x$$

FIG. 1 shows a graph depicting the typical volume of air within the lungs during a typical inhalation cycle of a patient. The tidal volume can vary, due to factors, such as, for example, the age of the patient, the health of the patient, the size of the patient, and the like. As used herein, the "tidal volume" refers to the lung volume representing the normal volume of air displaced between normal inhalation and exhalation when extra effort is not applied. Thus, tidal volume is the maximum volume taken in by the end of a normal relaxed inhalation. As a non-limiting example, in a healthy, young human adult, tidal volume is approximately 500 mL per inspiration or 7 mL/kg of body mass. Correspondingly, "minute volume", $\dot{V}_{MV}$, refers to the total inhaled volume per minute, equivalent to the tidal volume per breath times the breath rate per minute. For example, a patient breathing a tidal volume of 500 mL, and taking breaths 20 times a minute, would have a $\dot{V}_{MV}$ of 10 lpm (=20 per minute×500 mL).

FIG. 2 depicts the operation of a device according to some embodiments of the present invention during a typical respiration cycle of a patient. In FIG. 2, panel a), the patient is exhaling, and the check valve labeled "inhalation check valve" is closed, preventing gas exhaled by the patient from entering the at least one reservoir tube. Instead, the gas exhaled by the patient is exhausted from the system via the check valve labeled "exhalation check valve". The at least one therapeutic gas enters the system via an inlet port located on the reservoir side of the inhalation check valve at the proximal end of the at least one reservoir tube, and flows towards the distal end of the at least one reservoir tube which is open to a neutral pressure, in this case ambient room air.

In FIG. 2, panel b), the patient is inhaling and the check valve labeled "inhalation check valve" is open, allowing the at least one therapeutic gas within the at least one reservoir tube and simultaneously the at least one therapeutic gas entering the system via the inlet port at a rate $\dot{V}_a$ to enter the patient's airway. The check valve labeled "exhalation check valve" is closed, preventing the patient from inhaling ambient air. As the patient inhales, neutral pressure ambient air is drawn in and enters the distal end of the at least one reservoir tube. However, the at least one reservoir tube is configured to prevent the entering ambient air from unduly mixing with and diluting the at least one therapeutic gas present in the reservoir tube.

In FIG. 2, panel c), the patient is near the end of an inhalation cycle, and the check valve labeled "inhalation check valve" is still at least partially open, allowing the at least one therapeutic gas within the at least one reservoir tube and the at least one therapeutic gas entering the system via the inlet port to enter the patient's lungs. The check valve labeled "exhalation check valve" is closed, and still prevents the patient from inhaling ambient air. However, there is still a small volume of the at least one therapeutic gas remaining in the proximal end of the at least one reservoir tube. At this point in the patient's breathing cycle, the inhalation phase is just ending and the exhalation phase is just about to start.

In FIG. 2, panel d), the patient has transitioned to exhaling, and the check valve labeled "inhalation check valve" is closed, preventing gas from the patient's lungs entering the at least one reservoir tube. Instead, the gas exhaled by the patient, containing waste constituents of the at least one therapeutic gas, is exhausted from the system, via the check valve labeled "exhalation check valve". During exhalation, the at least one therapeutic gas continues to enter the system via the said inlet port, and the at least one therapeutic gas re-fills the at least one reservoir tube in preparation for the patient's next breath, with the re-fill action progressing from the proximal end of the at least one reservoir tube towards the distal end which is at a neutral pressure. The incoming fresh at least one therapeutic gas displaces the remaining residual therapeutic gas and ambient air remaining from the last inhalation cycle towards the distal end of the at least one reservoir tube, such that those are emptied from the at least one reservoir tube. In some embodiments, the at least one reservoir tube is refilled concurrently with the inhalation check valve being closed.

In some embodiments, the system of the present invention is configured to provide a safety mechanism to the patient, where the safety mechanism is configured to allow the patient to breath ambient air if entry of the therapeutic gas into the system is interrupted according to some embodiments of the present invention.

In some embodiments, the reservoir tube is "open" in the longitudinal direction (e.g., to two ends of the hose), but not along the perimeter of the shape describing its cross section. In some embodiments, the channel is not a "U" or other open sided shape that would allow air to enter along the side of the reservoir.

In some embodiments, the at least one therapeutic gas is a mixture of at least two gases, and the mixture of the at least two gases is inhaled by the patient using the system according to some embodiments of the present invention.

Thus, in some embodiments shown in FIGS. 2A-D, the therapeutic gas inhaled by the patient with an instantaneous amplitude $\dot{V}_{inhaled}$ comprises varying portions of the newly supplied therapeutic gas $\dot{V}_a$, and the therapeutic gas recently stored along the length of the at least one reservoir tube in preparation for the inhalation, since the instant amplitude of $\dot{V}_{inhaled}$ can significantly exceed the injected at least one therapeutic gas flow rate $\dot{V}_a$, typically by factors ranging from 2 to 5 (but not specifically limited to those values) However, the therapeutic gas stored in the reservoir and the newly supplied therapeutic gas have equivalent compositions so any blend of the two will result in a similar gas composition. Accordingly, the therapeutic gas inhaled by the patient has a consistent composition through each inhalation cycle, which is also substantially the same as the composition of the original injected therapeutic gas.

In some embodiments, $\dot{V}_a$ is configured to produce a small net-outflow of the at least one therapeutic gas from the distal end of the at least one reservoir tube. In some embodiments, the net outflow acts to expel the "oldest" residual gas fill remaining after the previous inhalation of the at least one therapeutic gas from the at least one reservoir tube, to reduce or eliminate the potential build up of toxic contaminants, such as, for example, NO2 in the at least one reservoir tube. Additionally, with a net outflow that tends to flush the at least one reservoir tube from one breath to the next, the patient will breath in a substantially consistent concentration of the at least one therapeutic gas. In this context a small net-outflow would be introduced by supplying the expected total minute volume $\dot{V}_{MV}$ (to supply the patient's breathing needs) plus a margin of something like 3% to 10% of the total minute volume to effect the desired small net-outflow flushing. In some embodiments, the measured concentration is steady within a few percent of the initial start up settings and is within 5% of the ideal 160 ppm concentration. In some embodiments, the calibration accuracy of the flow meters and gas analyzers used to assess the concentration during the treatment is about +/−3% at the disclosed concentration values, so a measure is how much the concentration varied with respect to itself over the course of a 30 minute treatment. In some embodiments, the treatment varied about 3% overall in the course of 30 minutes.

The system according to some embodiments of the present invention is adapted using a specific patient interface to deliver at least one therapeutic gas to a patient according to the patient's airway configuration. For example, in some embodiments, the patient inhales through the nose and exhales through the mouth, while in other embodiments, the patient inhales through the mouth and exhales through the nose. Also for example, the patient may inhale and exhale solely through either the mouth or the nose.

In some embodiments, the patient is trained to inhale through one airway opening, and exhale through a different airway opening. For example, a patient may be trained to inhale through the mouth, and exhale through the nose.

In some embodiments, the patient interface forms a gas-tight seal between the patient and the system.

In some embodiments, the patient interface is a patient interface selected from the group consisting of but not limited to: a full face mask, a nose mask, a mouthpiece, and a pillow seal nasal cannula.

In some embodiments, the system of the present invention is configured to provide an anti-suffocation feature, where the anti-suffocation feature comprises an open distal end of the at least one reservoir tube placed in a neutral pressure breathable atmosphere. In some embodiments, if the at least one therapeutic gas of the system stops entering the system, then the system is configured to allow a patient to inhale ambient air.

In some embodiments, the system of the present invention is configured to move the at least one therapeutic gas in the reservoir in a back and forth manner, e.g., a "first in, last out" movement that shuttles gas back and forth in the reservoir tube without significant longitudinal mixing.

In some embodiments, the patient interface is held in place by the patient. Alternatively, in some embodiments, the patient interface is attached to the patient, such as, for example, via an elastic strap that is positioned over the patient's head.

In some embodiments, the at least one reservoir tube has a smooth inner surface. In some embodiments, the at least one reservoir tube has a rough inner surface.

In some embodiments the at least one reservoir tube has a uniform cross-section along its length.

Figure 3:
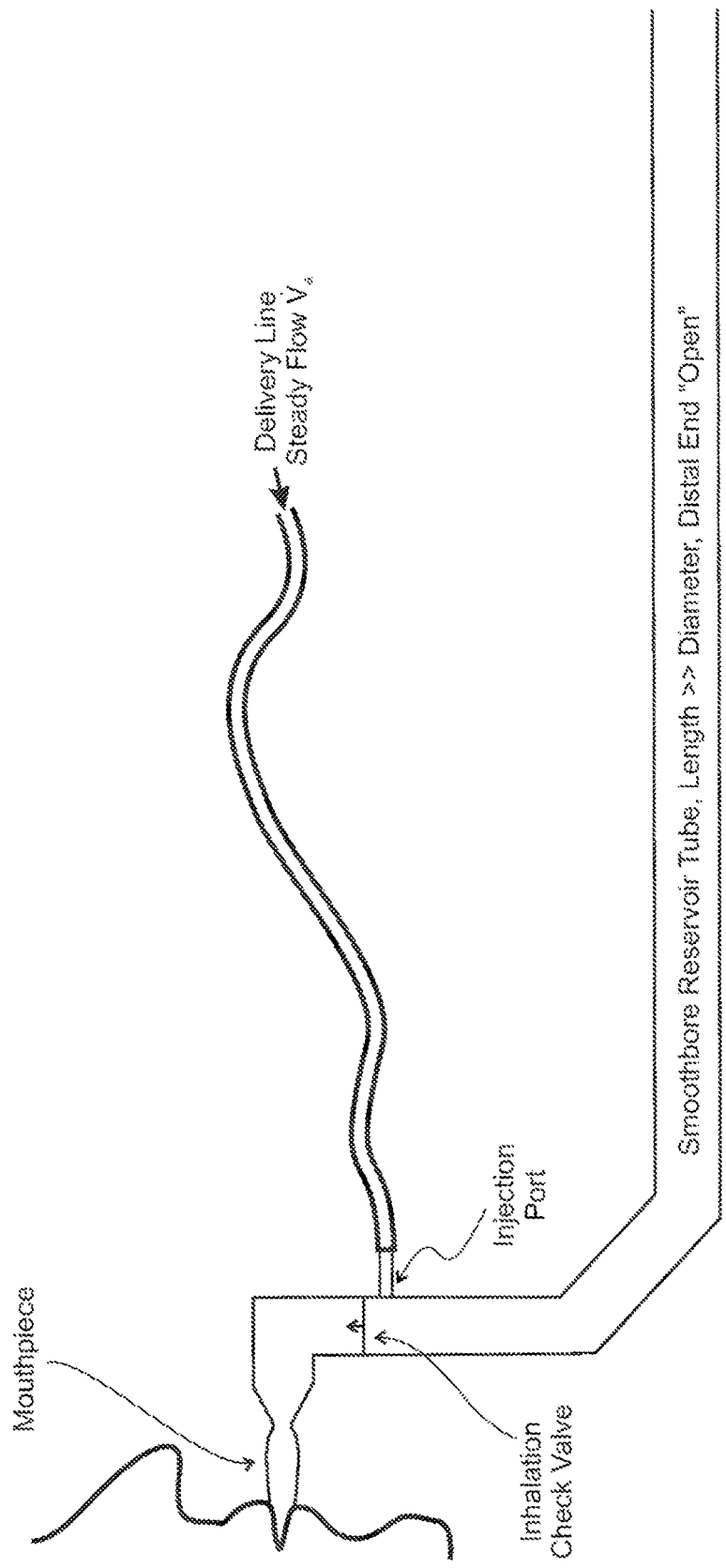
FIG. 3 shows a gas delivery system according to some embodiments of the present invention, where the patient breathes from the proximal end of a reservoir through a mouthpiece.

In one example, referring to FIG. 3, in some embodiments, the present invention provides a system configured to administer at least one therapeutic gas to a patient, comprising:
  a. at least one reservoir tube, having a proximal and distal end, wherein the at least one reservoir tube has a volume larger than the tidal volume of the patient;
  b. at least one therapeutic gas inlet at the proximal end of the at least one reservoir tube, wherein a delivery tube is connected to the at least one therapeutic gas inlet and at least one therapeutic gas source; and
  c. a patient interface fluidly connected to the proximal end of the at least one reservoir tube via a check valve,
    wherein the patient interface is configured to form a gas-tight seal between the patient and the system,
    wherein the patient interface is a mouthpiece configured to form a gas-tight seal when the patient purses their lips,
    wherein the inhalation check valve is configured to be closed when the patient is exhaling,
    wherein the at least one therapeutic gas is introduced into the at least one reservoir tube at the proximal end through the at least one therapeutic gas inlet at a rate greater than the patient minute volume, and the at least one therapeutic gas flows along the at least one reservoir tube, from the proximal end towards the distal end whilst the patient is exhaling,
    wherein the check valve is configured to be open when the patient is inhaling, and allow the at least one therapeutic gas to be administered to the patient.

Further, in FIG. 3, the check valve may be removed and the system is configured to allow the patient to breathe through his mouth and exhale through his nose. Accordingly, in this exemplary embodiment, the patient affects the inhalation check valve functionality.

Figure 4:
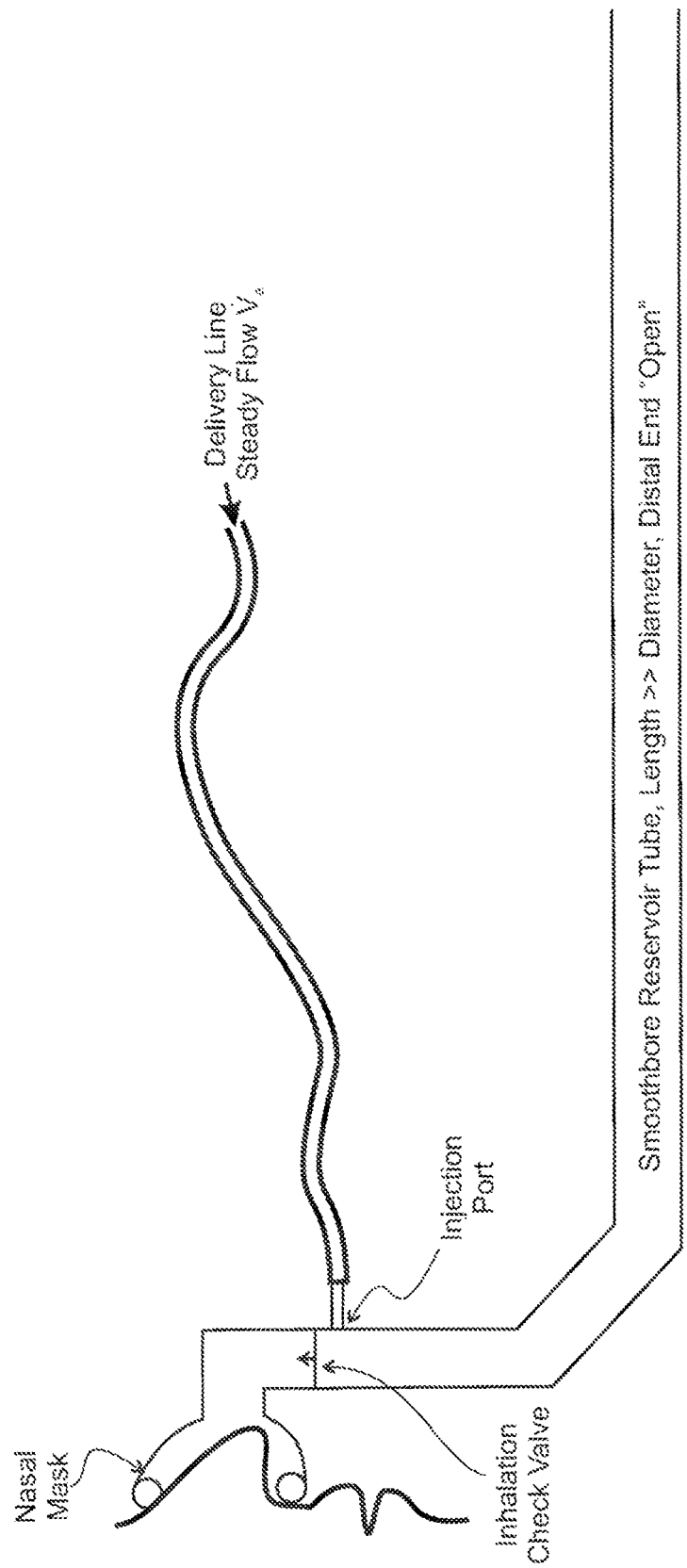
FIG. 4 shows a gas delivery system according to some embodiments of the present invention, where the patient breaths from a nasal mask.

In another example, referring to FIG. 4, in some embodiments, the present invention provides a system configured to administer at least one therapeutic gas to a patient, comprising:
- a. at least one reservoir tube, having a proximal and a distal end, wherein the at least one reservoir tube has a volume larger than the tidal volume of the patient;
- b. at least one therapeutic gas inlet at the proximal end of the at least one reservoir tube, wherein a delivery tube is connected to the at least one therapeutic gas inlet and at least one therapeutic gas source; and
- c. a patient interface fluidly connected to the proximal end of the at least one reservoir tube via a check valve,
  wherein the patient interface is configured to form a gas-tight seal between the patient and the system,
  wherein the patient interface is a nose mask configured to form a gas-tight seal when placed over the patient's nose,
  wherein the check valve is configured to be closed when the patient is exhaling,
  wherein the at least one therapeutic gas is introduced into the at least one reservoir tube at the proximal end through the at least one therapeutic gas inlet at a rate greater than the patient minute volume, and the at least one therapeutic gas flows along the at least one reservoir tube, from the proximal end to the distal end whilst the patient is exhaling,
  wherein the check valve is configured to be open when the patient is inhaling, and allow the at least one therapeutic gas to be administered to the patient.

Figure 5A:
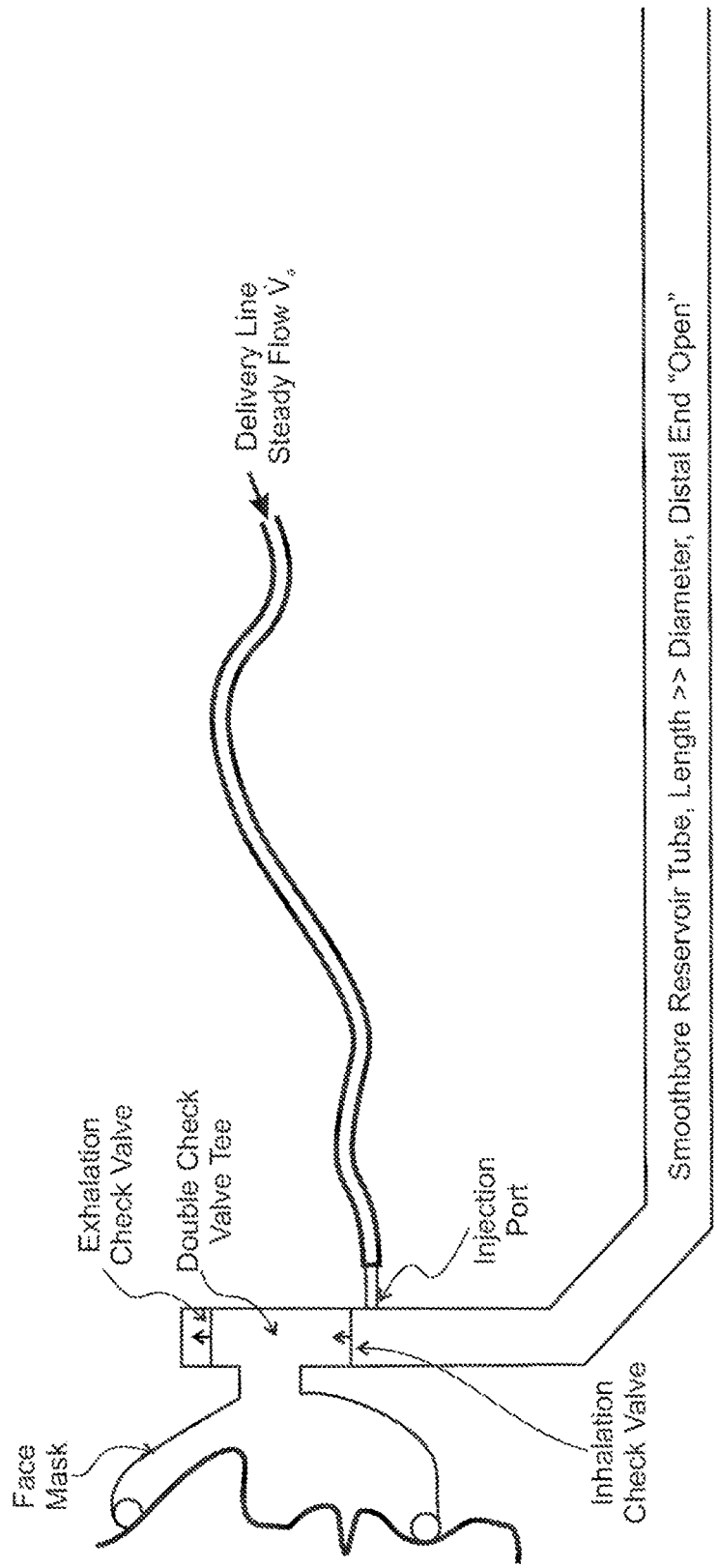
FIGS. 5(a) and 5(b) show a gas delivery system according to some embodiments of the present invention, where the gas delivery system is configured with both an inhalation check valve and an exhalation check valve. Alternative patient connections are pictured in FIG. 5(a) and FIG. 5(b).

In another example, referring to FIG. 5A, in some embodiments, the present invention provides a system configured to administer at least one therapeutic gas to a patient, comprising:
- a. at least one reservoir tube, having a proximal and a distal end, wherein the at least one reservoir tube has a volume larger than the tidal volume of the patient;
- b. at least one therapeutic gas inlet at the proximal end of the at least one reservoir tube, wherein a delivery tube is connected to the at least one therapeutic gas inlet and at least one therapeutic gas source; and
- c. a patient interface fluidly connected to the proximal end of the at least one reservoir tube via a first check valve,
  wherein the patient interface is configured to form a gas-tight seal between the patient and the system,
  wherein the patient interface is a face mask that covers the patient's mouth and nose, and is configured to form a gas-tight seal when placed over the patient's nose and mouth,
  wherein the first check valve is configured to be closed when the patient is exhaling,
  wherein the at least one therapeutic gas is introduced into the at least one reservoir tube at the proximal end through the at least one therapeutic gas inlet at a rate greater than the patient minute volume, and the at least one therapeutic gas flows along the at least one reservoir tube, from the proximal end to the distal end, whilst the patient is exhaling,
  wherein the volume of the at least one therapeutic gas that is introduced into the at least one reservoir tube whilst the patient is exhaling, is greater than the patient's tidal volume,
  wherein the first check valve is configured to be open when the patient is inhaling, and allow the at least one therapeutic gas to be administered to the patient,
  wherein the patient interface is further configured with a second check valve, wherein the second check valve is configured to be closed when the patient is inhaling, and open when the patient is exhaling, and
  wherein the second check valve allows the gas exhaled by the patient to exit the system.

Figure 5B:
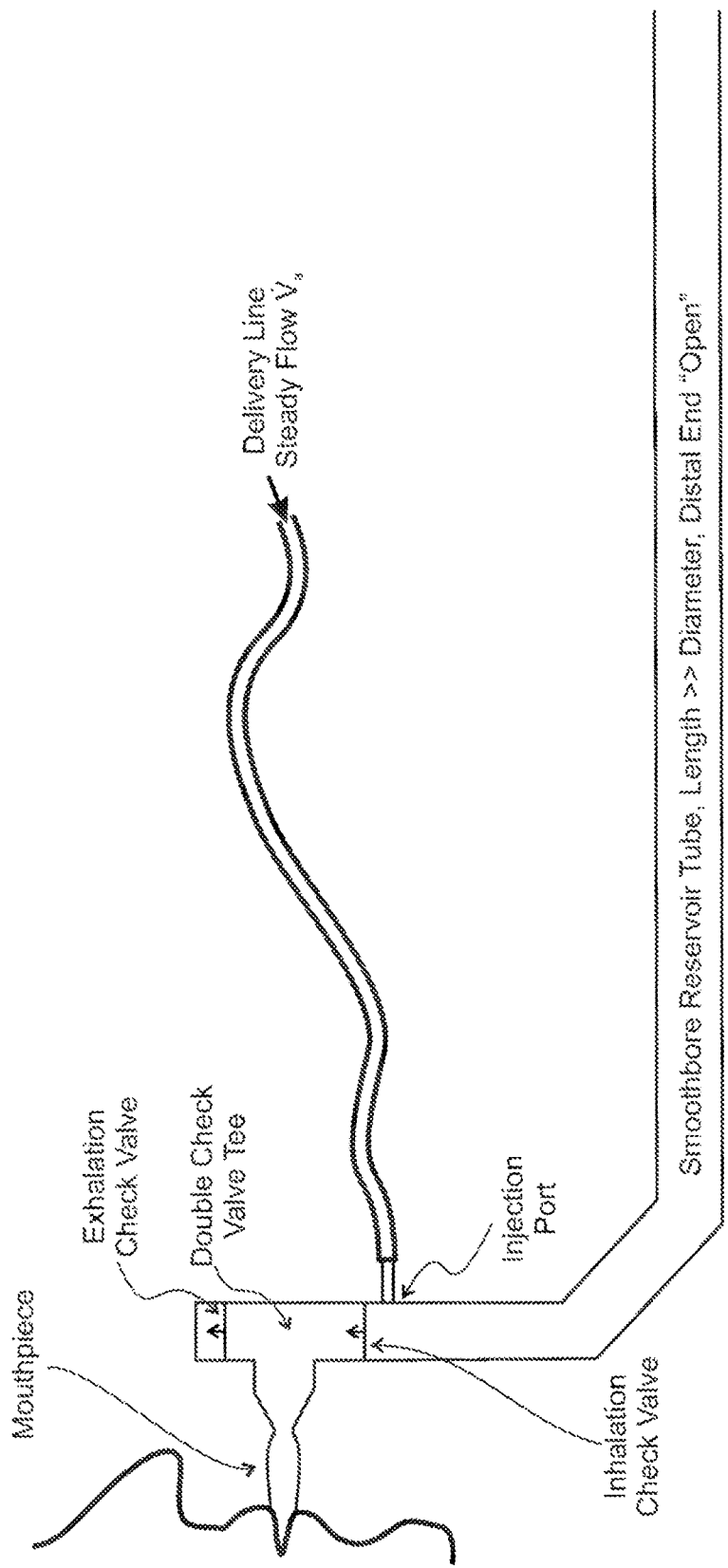

In some embodiments, the system of the present invention is configured to deliver the at least one therapeutic gas or the at least one diagnostic gas via a mouthpiece as shown, e.g., in FIG. 5b.

In some embodiments, the system of the present invention is configured to deliver an approximately constant mixture of diagnostic or therapeutic gases in combination with other diluting breathable gases to a spontaneously breathing patient during the inhalation portion of a breath:
  wherein the flow of each constituent source gas that is part of the final mixture can be set at a constant rate appropriate to the desired end concentration in the final inhaled mixture; and
  wherein such source gases inject individually or jointly to one or more junctures ultimately feeding the proximal end of a reservoir, the reservoir providing a temporary storage location for any inflow not required by a patient inhalation, such reservoir having a high length to cross-section aspect ratio that effectively shuttles gas along the length of the reservoir without undue mixing of the gas in the longitudinal flow direction; and
  a means to attach the proximal end of the reservoir to a patient's airway so that the patient can freely inhale from the convergence of the proximal end of the reservoir and the injected source gases, but any patient exhalation is prevented from flowing back into the reservoir; and
  wherein the distal end of said conducting reservoir is open to a neutral pressure region where substantially clean breathable air exists.

In some embodiments, the sum of the individual constant source rate flows exceeds the time averaged patient inhalation flow and thus a net outflow of gas is present at the distal end of the reservoir. This excess is shown formulaically as $$\dot{V}_a = \sum_n \dot{V}_x > \dot{V}_{MV}.$$

In some embodiments, the net outflow or inflow of gas at the distal end of the reservoir is monitored to ensure that effectively no ambient air is normally inhaled by the patient, which in this case is shown formulaically as $$\dot{V}_a = \sum_n \dot{V}_x = \dot{V}_{MV}.$$

In this case as well, a minimum of the at least one therapeutic gas is required to effect the patient treatment, but the open distal end of the at least one reservoir tube preserves the anti-suffocation feature.

In some embodiments, the volume of the reservoir is slightly larger than the typical tidal volume of the patient.

In some embodiments, the sum of the individual constant source rate flows exceeds the time averaged patient inhalation flow and thus a net outflow of gas is present at the distal end of the reservoir.

In some embodiments, the sum of the individual constant source rate flows exceeds the time averaged patient inhalation flow by a small fraction and thus a net outflow of gas is present at the distal end of the reservoir to flush the reservoir of older gas.

In some embodiments, the net outflow or inflow of gas at the distal end of the reservoir is monitored by a flow meter.

In some embodiments, the therapeutic or diagnostic source gas contains Nitric Oxide in a concentration higher than the required for effective patient delivery, such gas to be diluted with diluent gas and delivered by the device at a fixed concentration selected between 400 ppm to 0.5 ppm with the balance being air or air enriched with oxygen.

In some embodiments, more than one type of therapeutic or diagnostic gas is blended through additional injection points to achieve fixed concentrations of more than one target gas during the same patient inhalation.

In some embodiments, the means to prevent back flow of any exhaled patient breaths into the at least one reservoir tube is provided by a directional flow check valve positioned between the patient's airway and the combined proximal outlet of the reservoir tube and the source gas injection points.

In some embodiments, the means to prevent back flow of the patients exhaled breath into the reservoir is accomplished by the patients trained breathing pattern wherein they alternately breath in through only one of the mouth or nose, but not both, and then alternately breath out through the other, but again not both.

In some embodiments, the reservoir is formed from a single long channel with sufficient volume to equal or exceed the tidal volume of the patient, but simultaneously of sufficient cross-section to result in low breathing effort.

In some embodiments, the reservoir may be smaller than a patient's tidal volume, but only if sufficient injected flow $\dot{V}_a$ is provided to supply enough of the required $\dot{V}_{inhaled}$ flow during the patient's inhalation such that the gas stored in the at least one reservoir tube is not exhausted before the end of the patient's inhalation.

In some embodiments, the reservoir is formed from a plurality of parallel flow channels that each individually present a high length to cross-sectional dimension aspect, so that each individual channel shuttles any gas flowing in the channel in a way that suppresses longitudinal mixing of the gas, but where the parallel ensemble provides a total volume sufficient to equal or exceed a patient's tidal volume.

In some embodiments, the present invention is a delivery device configured to provide a breathable mix of gases including therapeutic or diagnostic gases and diluting gases and where a constant ratio of constituents is desired during inhalation by a spontaneously breathing patient, wherein one or more constant flow supplies of therapeutic or diagnostic source gases and diluting gases are injected into one or more adjacent gas ports located at the proximal end of a reservoir,
- the reservoir is formed from one or a plurality of parallel channels that are long compared to their cross-sectional dimensions,
- the distal end of the reservoir is open to a source of ambient pressure breathable gas,
- the net volume of the reservoir is equal to or larger than a patient's inhaled tidal volume,
- the total of all the injected flows of therapeutic and diluting gases equals or exceeds the patient's minute volume flow rate, and
- the proximal end of the reservoir and gas injection ports are connected to a conduit connecting to the patient's airway with an air-tight seal.

In some embodiments, the patient's airway is separated from the proximal end of the reservoir and gas injection points by a directional flow check valve.

In some embodiments, any injected flow that exceeds the patient's minute volume exhausts from the distal end of the reservoir without restriction.

In some embodiments, one of the injected constant gas flows carries a fixed proportion of Nitric Oxide, said Nitric Oxide in the inject flow being at a concentration higher than that required for the patient treatment, and where the final blended Nitric Oxide concentration for patient treatment is adjustable in the range between 400 ppm to 0.5 ppm delivered in a diluting balance of air or oxygen enriched air.

In some embodiments, the diagnostic gas comprises a tracer gas, e.g., including but not limited to helium, hydrogen, sulfur hexafluoride, carbon monoxide or combinations thereof.

In some embodiments, the device is equipped with a flow port with an outward facing flow check valve to exhaust the patient's exhaled breath.

In some embodiments, the distal end of the reservoir is equipped with a flow monitor that allows the net flow of gas into and out from the distal end of the reservoir to be assessed. In some embodiments, the distal flow assessment can be performed automatically, or manually, or any combination thereof.

In some embodiments, the device of the present invention further comprises at least one alarm, at least one monitor, or any combination thereof, including but not limited to those related to constituent gas flows, gas concentrations, total flows, total volumes, contamination levels, humidity, temperature, time or any combination thereof.

In some embodiments, the at least one monitor is configured to notify at least one entity (e.g., but not limited to, a caregiver (e.g., but not limited to, a doctor, a nurse, a parent, etc.), a medical provider, a cognisant patient, etc.), if at least one of the following conditions is met: if the sum of the individual constant source rate flows does not exceed the time averaged patient inhalation flow, if the net outflow or inflow of gas at the distal end of the reservoir allows for the inhalation of ambient air by the patient, if the volume of the reservoir is depleted during the course of a typical inhalation by the patient, if the sum of the individual constant source rate flows does not exceed the time averaged patient inhalation flow by a small fraction, if the fixed concentration does not lie within a predetermined range set as part of the intended therapy, if the back flow of patient's breaths is detected, if the total duration of the therapy is lower or higher than the prescribed time by some predetermined margin, or any combination thereof. In some embodiments, the at least one alarm is configured to alert at least one entity (e.g., a caregiver, a medical provider, etc.) if the at least one monitor identifies at least one of the conditions as described herein.

In some embodiments, the device of the present invention can be used to treat a single subject or reused for multiple subjects in turn. In some embodiments, the treatment can be in a hospital setting or outside of a hospital setting (e.g., but not limited to, in a home, an airport, a mall, a public health clinic, a quarantine facility, etc.).

Figure 6:
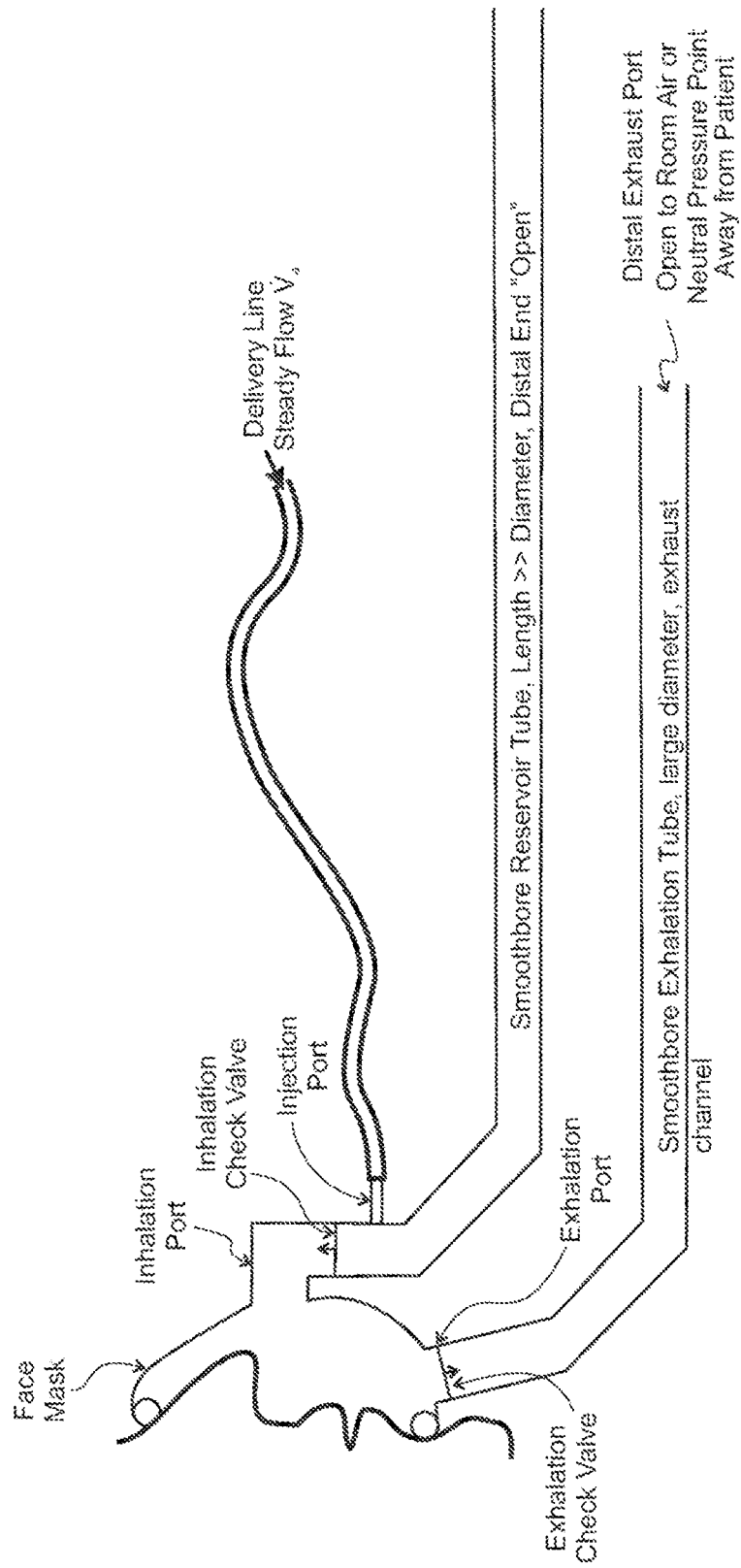
FIG. 6 shows a gas delivery system according to some embodiments of the present invention, where the delivery system is configured with both inhalation and exhalation check valves and an exhalation exhaust tube to route exhaust away from the patient.

In some embodiments, an exhaust collecting conduit may be required as shown in FIG. 6, to convey the exhaled gas to an analysis, venting, disposal or decontamination region.

In some embodiments, the composition of the exhaled gas may be analyzed to assess the patient's uptake of a component of the therapeutic or diagnostic tracer gas, or alternatively a residual component of the therapeutic gas. In some embodiments, the exhaled gas may contain contaminants that require treatment prior to entering the environment. For instance, exhaled residual components and contaminants may include gases such as NO that was not absorbed, NO2 produced as a byproduct of NO, infectious particulates, or radioactive materials.

The at Least One Reservoir Tube

Typical tidal volumes for human patients range from 3 ml/kg (e.g., but not limited to, a small child) to 5 ml/kg (e.g., but not limited to, an adult) body weight. In some embodiments, typical tidal volumes for human patients range from 50 mL (e.g., but not limited to, a small child) to 750 mL (e.g., but not limited to, a large adult).

In some embodiments, the at least one reservoir tube is configured to hold a sufficient volume of the at least one therapeutic gas to support the flow during a patient inhalation. In some embodiments, the sufficient volume of the at least one therapeutic gas is equal to the tidal volume of the patient. In some embodiments, the sufficient volume is equal to 100%+x % of the tidal volume of the patient, where x % is a fraction of a tidal volume (e.g., but not limited to, 10%), thus the reservoir in that case would be sized to store 110% of the tidal volume for that patient. In some embodiments, the length and thus volume of the at least one reservoir tube is intended to be adjusted to match the characteristics of a particular patient. In some embodiments, the injected flow is intended to be adjusted to match the characteristics of the particular patient. In some embodiments both the at least one reservoir tube volume and the injected flow $\dot{V}_a$ are intended to be adjusted to match the characteristics of a particular patient.

In some embodiments, the at least one reservoir tube comprises a tube, having a smooth inner wall surface and a high length to cross-sectional dimension ratio. In some embodiments, the at least one reservoir tube has a sufficiently round aspect and an equivalent internal diameter, wherein the equivalent diameter is a small fraction of the reservoir length (e.g., but not limited to, between 0.5% and 5% of the reservoir length.

Thus, by way of illustration, for a 100 kg patient, having a tidal volume of 500 mL, using an at least one reservoir tube having a 19 mm internal diameter, the length of the at least one reservoir tube to hold 550 mL (e.g., a reservoir volume margin 10% above the tidal volume) can be calculated as follows:

| Symbol | Description | Units |
|---|---|---|
| $D_R$ | Internal diameter of the reservoir tube | [mm] |
| $A_R$ | Cross-sectional area of the reservoir tube | [mm$^2$] |
| $L_R$ | Length of reservoir tube | [m] |
| $V_R$ | Internal volume of the reservoir tube | [litre] |

$D_R = 3/4" = 19$ mm $A_R = \frac{\pi D_R^2}{4} = 283.5$ mm$^2$ $V_R = 500$ mL $= 0.5$ L $L_R = \frac{V_R}{A_R} = 1.76$ m Therefore, a 1.76 meter reservoir tube with a 19 mm internal diameter will give a reservoir internal volume of 500 mL. To create the 10% margin volume, the length must be increased to 1.94 meters (which increased the reservoir to 550 mL).

Figure 7:
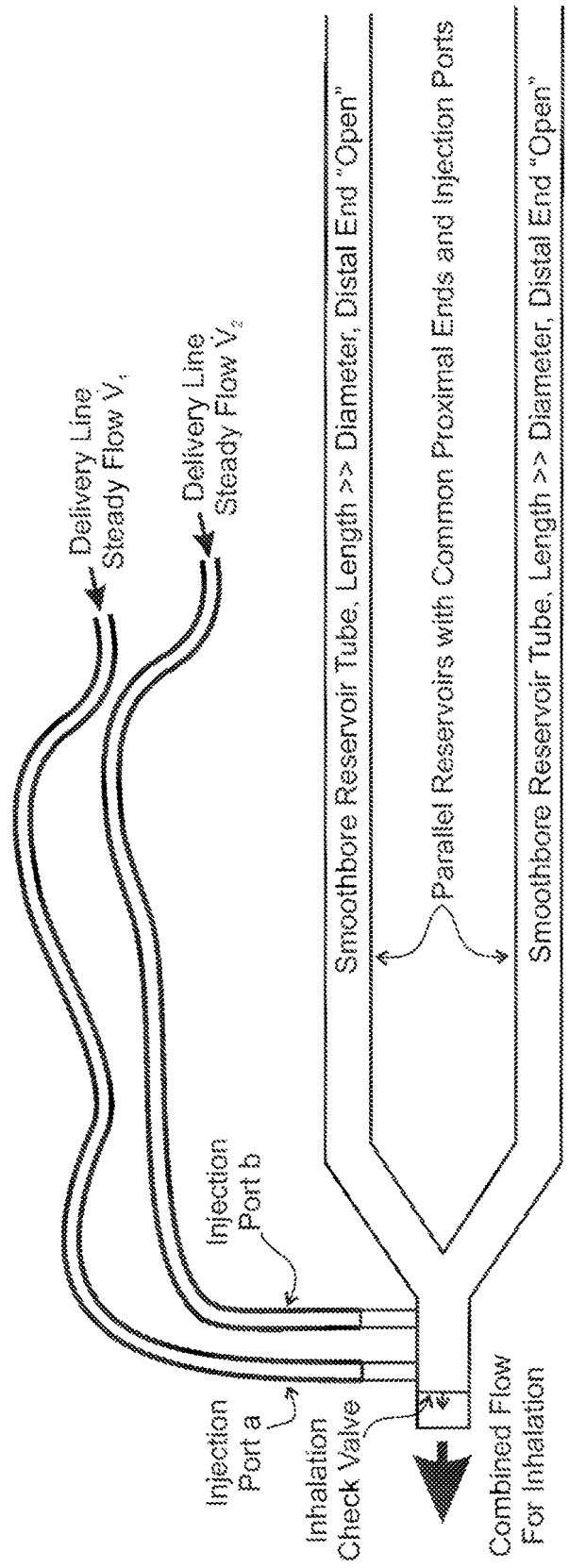
FIG. 7 shows a gas delivery system according to some embodiments of the present invention, where the therapeutic gas contains two components that are delivered separately to the proximal end of the reservoir and injected separately into the reservoir.
Figure 8:
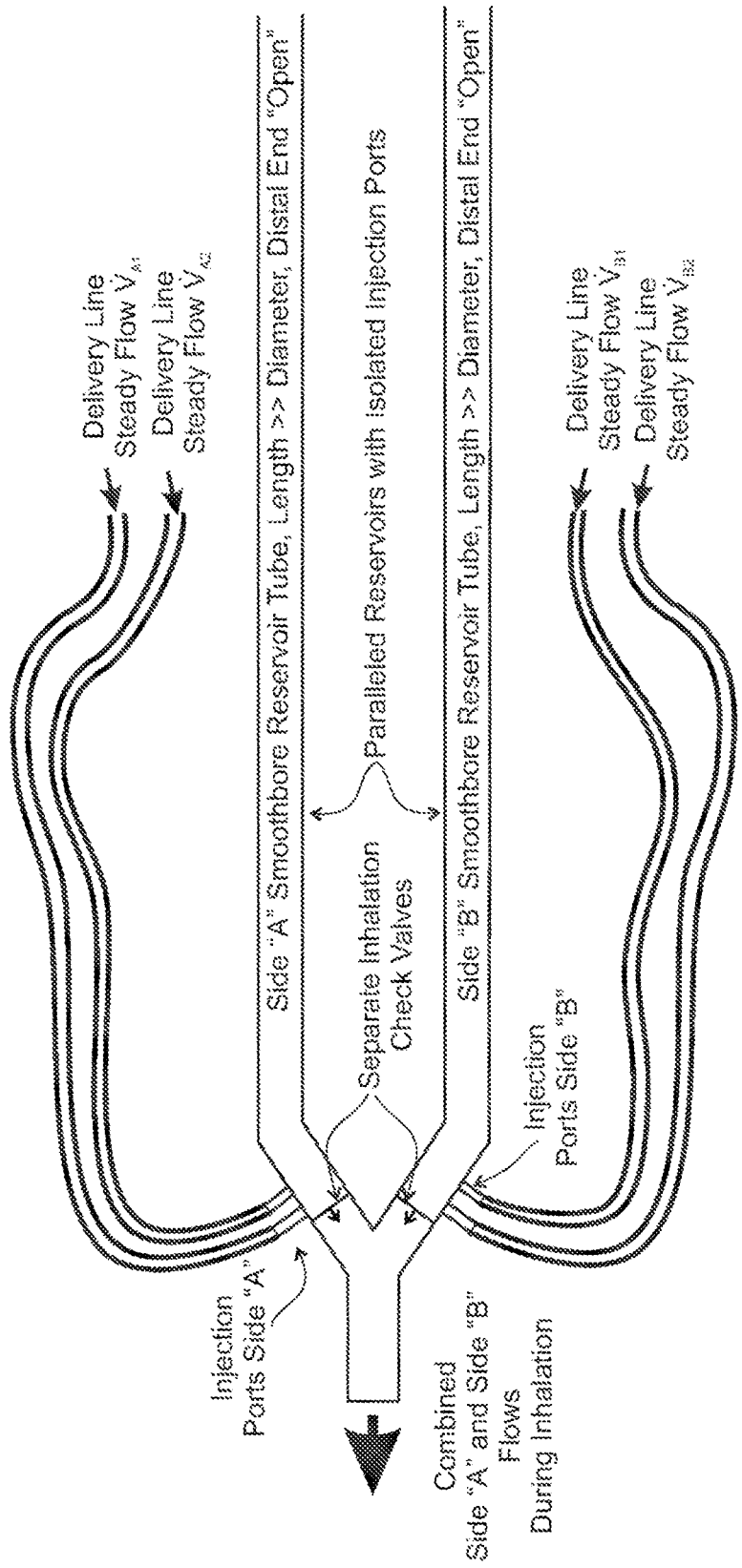
FIG. 8 shows a gas delivery system according to some embodiments of the present invention, where the reservoir is formed from more than one tube and more than one gas is brought separately to the reservoir.
Figure 9:
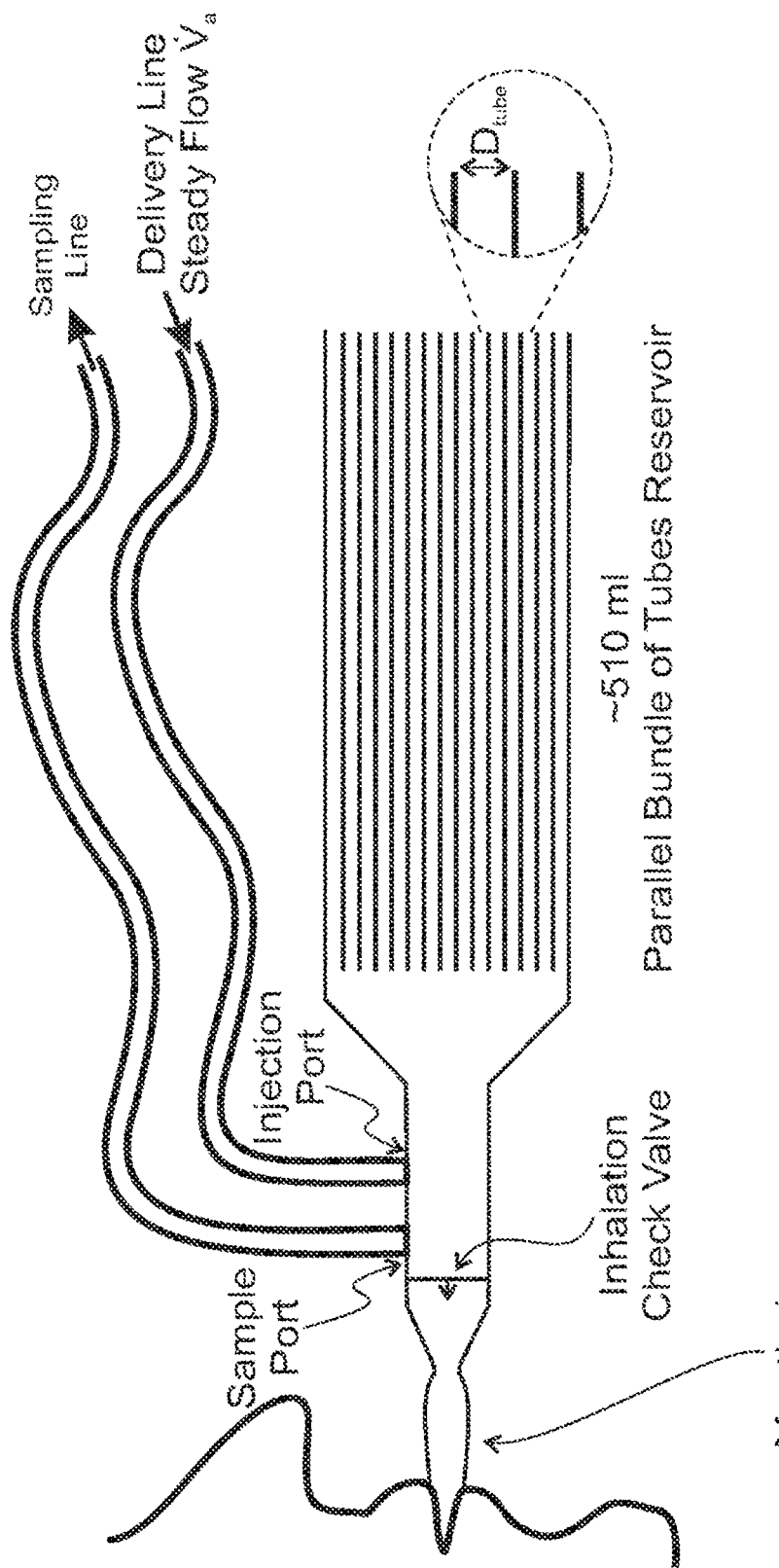
FIG. 9 shows a gas delivery system according to some embodiments of the present invention, where the reservoir is made from a plurality of small tubes providing the required total volume. This figure also introduces both a sample port and a sample line through which a small amount of the gas present at the proximal end of the reservoir can be withdrawn for analysis and monitoring. This sample port is located just distal to the inhalation valve so that it is effectively isolated from the patient exhalation.

In some embodiments, a number of tubes operating in parallel can form the reservoir and can be shorter in total length while still holding a sufficient volume of the at least one therapeutic gas. These parallel tube arrangements can include two parallel tubes or extend to many smaller diameter parallel tubes. Examples of these embodiments are shown in FIGS. 7 to 9. In these examples each tube in its own right presents a high length to cross-sectional dimension ratio, while the assembly in general gets shorter.

Thus, by way of illustration, for a 100 kg patient having a tidal volume of 500 ml, and using an at least one reservoir tube having a 19 mm internal diameter configured for a total reservoir volume $V_R$ of 510 mL (in this example, this represents a 2% margin over the tidal volume), if more than one reservoir tube can be used, the reservoir configuration can be determined as follows:

The length of the tubes is a function of the number of tubes used and the internal diameter of each tube. For instance, if a desired reservoir volume $V_R$ of 510 mL and the number N of similar round tubes is 30, each with an internal diameter $D_{tube}$ of 6 mm is selected, then the length of each small tube is determined as:

$$L_R = \frac{V_R}{N * \frac{\pi \cdot D_{tube}^2}{4}}$$

$$L_R = \frac{0.51 \text{L}}{30 * \pi * \frac{(4\text{mm})^2}{4}} = 0.60 \text{m}$$

Thus, a "bundle of straws" configuration can be constructed as indicated in FIG. 9.

In some embodiments, the rate at which the sufficient amount of the at least one therapeutic gas is introduced into the at least one reservoir tube is configured to introduce the sufficient amount during the exhalation phase of the patient's breathing cycle. In some embodiments, the rate at which the sufficient amount of the at least one therapeutic gas is introduced into the at least one reservoir tube is configured to introduce the sufficient amount in about 2 seconds when a patient breathes 30 times a minute.

In some embodiments, the reservoir volume must equal or gently exceed (e.g., up to 10%) the tidal volume of the patient's exhalation. In some embodiments, the incoming therapeutic gas flow rate total must equal or gently exceed the patient volume. In an exemplary embodiment, a patient's breathing pattern is used to guide the system of the present invention, where the patient has a 500 mL tidal volume and the patient breathes 30 times per minute, and where the reservoir volume is 510 mL. Thus, the patient minute volume $\dot{V}_{MV}$ is equal to (500 mL/breath×30 breaths/minute), or 15 liters per minute (LPM). Accordingly, the $\dot{V}_a$ should be set to the marginally increased level of (510 mL×30 breaths/minute) or 15.3 LPM.

The introduction of the at least one therapeutic gas into the at least one reservoir tube should be performed at a rate that does not induce turbulence, but invokes a bulk flow of the gas along the length of the reservoir. In some embodiments, the gas introduction is performed at a rate at which the flow of the at least one therapeutic gas is laminar. Thus, in some embodiments, the inner cross-section dimensions of the at least one reservoir tube and/or the inner surface texture of the at least one reservoir tube is selected to enable the flow of the at least one therapeutic gas to remain laminar along the reservoir length.

For example, by way of illustration, the Reynolds number is an indication of the laminar or turbulent nature of the flow of a gas. Reynolds numbers less than 2,300 are considered to be laminar flow. For flow in a pipe or tube, the Reynolds number, Re, is generally defined as:

$$Re = \frac{\rho v D_H}{\mu} = \frac{v D_H}{\upsilon} = \frac{\dot{V} D_H}{\upsilon A}$$

Where:

| Symbol | Description | Units |
| --- | --- | --- |
| $D_H$ | The hydraulic diameter (equivalent round pipe diameter) | [m] |
| $\dot{V}$ | The volumetric flow rate | [m³/sec] |
| A | The pipe cross-sectional area | [m²] |
| v | The mean velocity of the fluid | [m/sec] |
| μ | The dynamic viscosity of the fluid | [kg/(m · s)] |
| υ | The kinematic viscosity (=μ/ρ) | [m²/sec] |
| ρ | The density of the fluid | [kg/m³] |

Accordingly, in this exemplary embodiment, with a 19 mm reservoir tube and an assumed flow of 16 LPM in the reservoir tube (rounded up from the $\dot{V}$ from before), gives the following result during reservoir filling:

$$D_H = 19 \text{mm}$$

$$\dot{V} = 16 LPM = 0.000267 \text{m}^3/\text{sec}$$

$$A = 283.8 \text{mm}^2 = 2.835 * 10^{-4} \text{m}^2$$

$$v = 1.55 * 10^{-5} \text{m}^2/\text{sec}$$

$$Re = \frac{0.00028 * 0.019}{1.55 * 10^{-5} * 2.835 * 10^{-4}} = 1224.96$$

Thus, in this example, having a reservoir filling rate of 16 LPM results in a Re value in the laminar flow regime. In some embodiments, the flow of the at least one therapeutic gas in the at least one reservoir tube during the inhalation phase is also still laminar. By way of illustration, assuming the patient breathes with a peak inspiratory flow rate of about 40 LPM (taking in the 500 mL in about 0.75 sec and referencing the cyclical flow pattern of FIG. 1) and following similar calculations to the previous example, the demand on the reservoir will be about 24 LPM during the inspiration (that is, the 40 LPM inspiratory flow less the 16 LPM supplied directly by the injection flow of therapeutic gas). Thus the induced reservoir flow rate relates to a Reynolds number of about 1730, which is still within the range considered to be laminar.

In some embodiments, the at least one reservoir tube is coiled. The flow inside coiled tubes tends to remain in the viscous regime at higher flows for equivalent Re values than that for straight tubes. The curvature-induced helical vortices (Dean Vortex) tend to suppress the onset of turbulence and delay transition out of laminar flow. The critical Reynolds Number, $Re_{cr}$, which describes the transition from laminar to turbulent flow can be calculated by:

$$Re_{cr} = 2100 * \left(1 + 12\sqrt{\frac{0.5 * D_R}{R_{coil}}}\right)$$

Where:

| Symbol | Description | Units |
| --- | --- | --- |
| $Re_{cr}$ | Critical Reynolds number | None |
| $D_R$ | Internal diameter of the reservoir tube | [mm] |
| $R_{coil}$ | Coil radius of curvature | [mm] |

Figure 10:
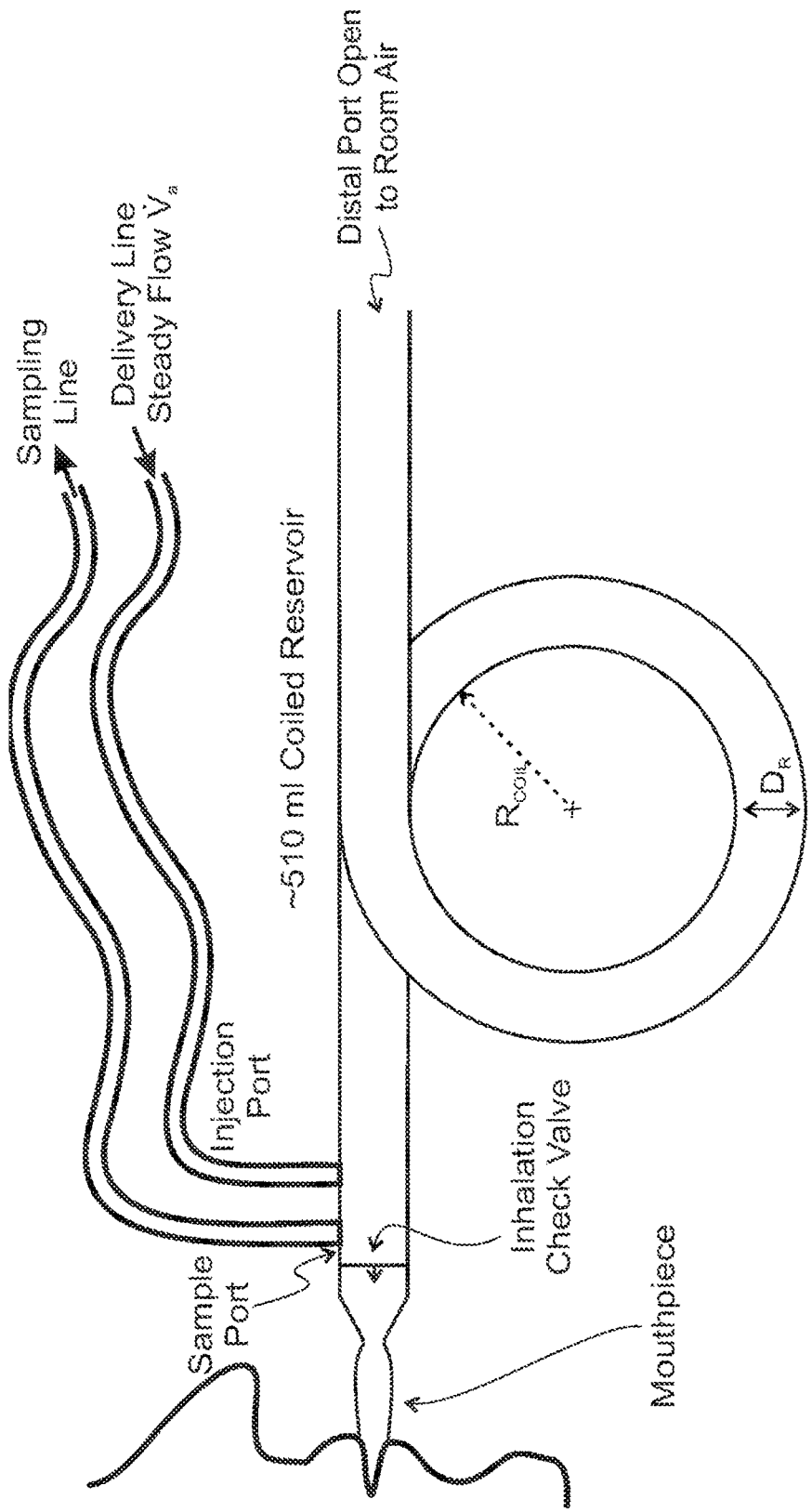
FIG. 10 shows a gas delivery system according to some embodiments of the present invention, where the long reservoir tube is coiled to reduce its physical size.
Figure 11:
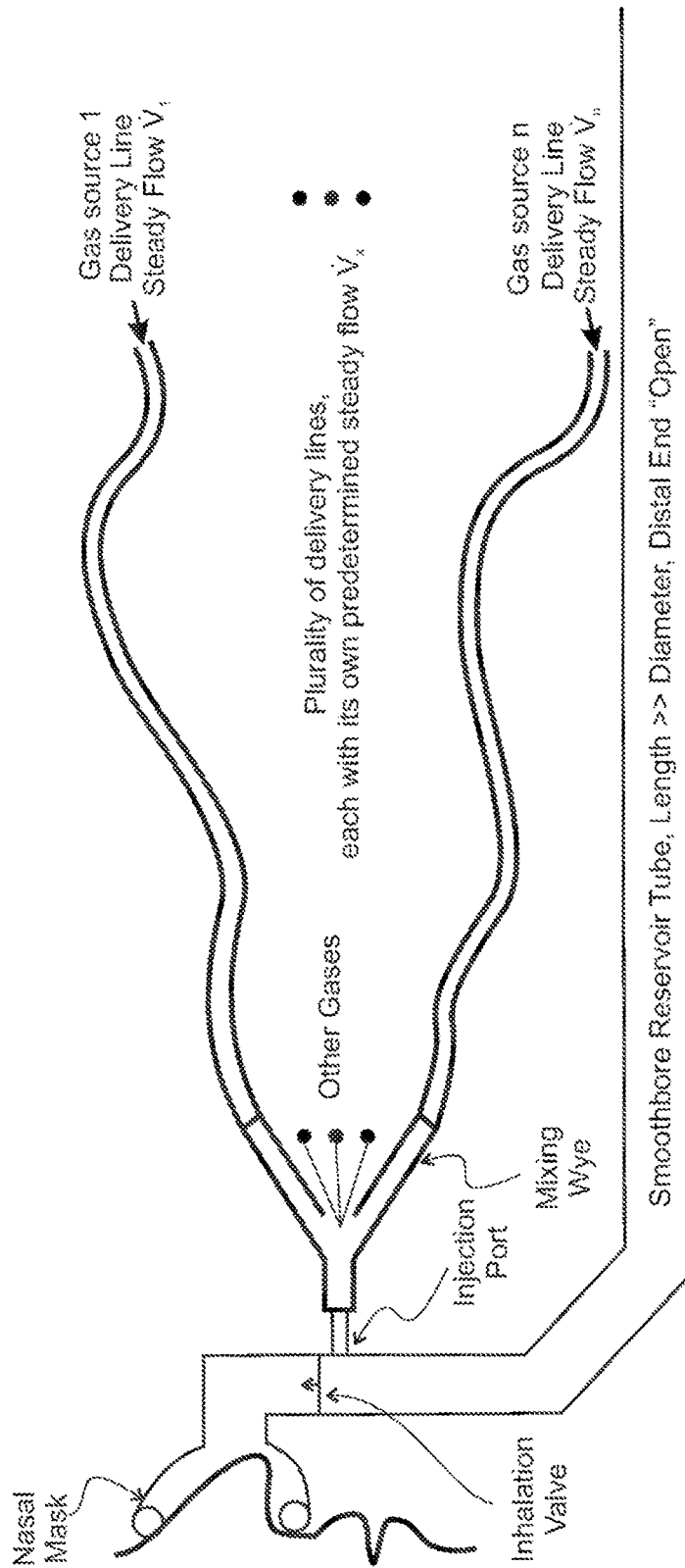
FIGS. 11 to 14 show gas delivery systems according to some embodiments of the present invention, where multiple source gases forming a final therapeutic blend are mixed prior to injection into the proximal end of the reservoir.
Figure 12:
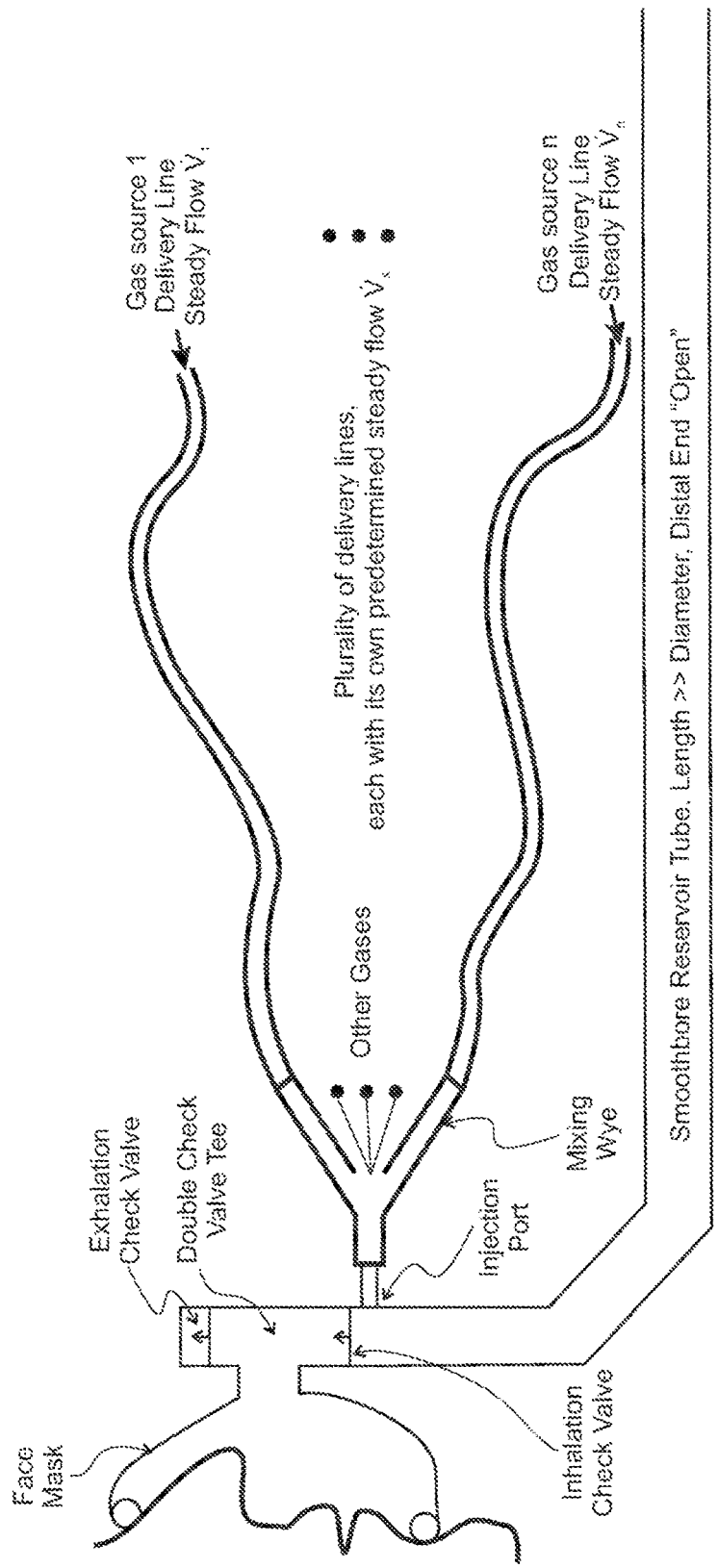
Figure 13:
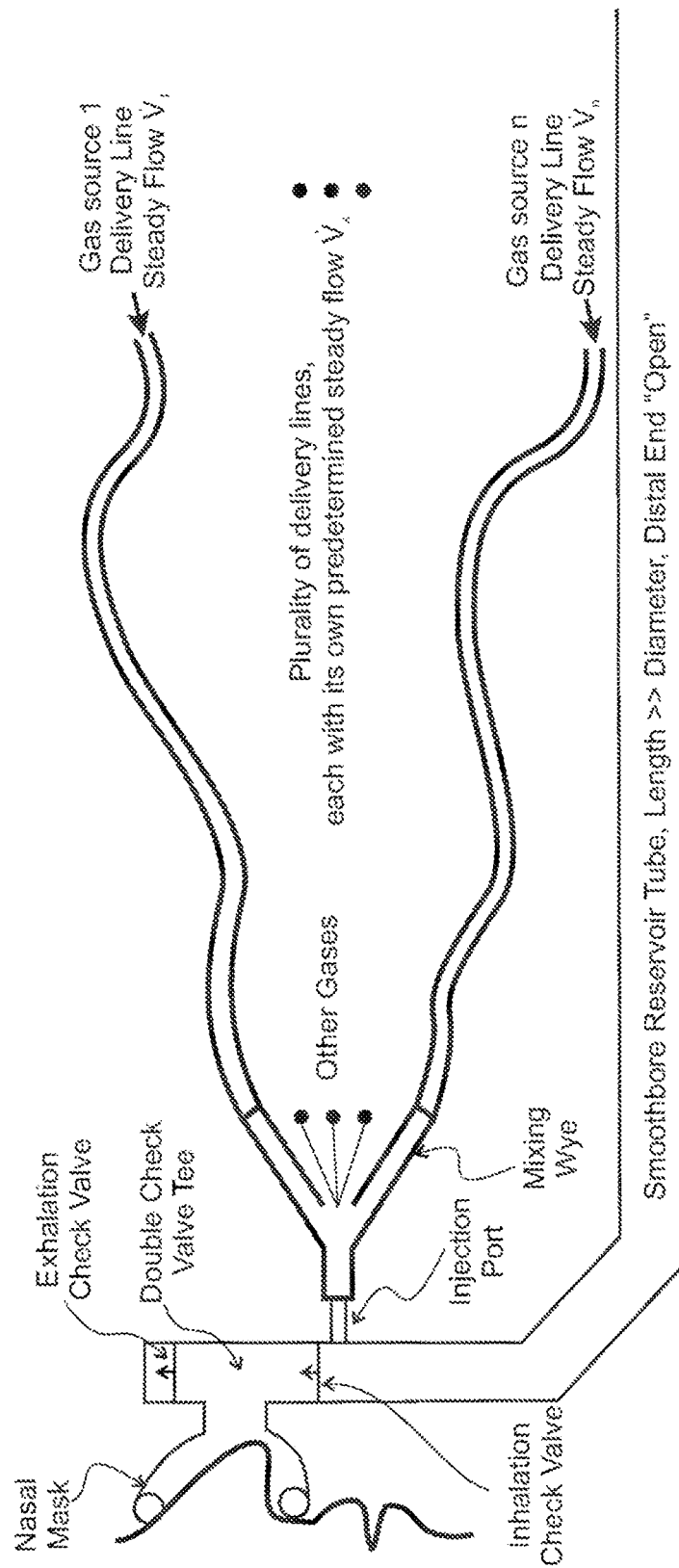
Figure 14:
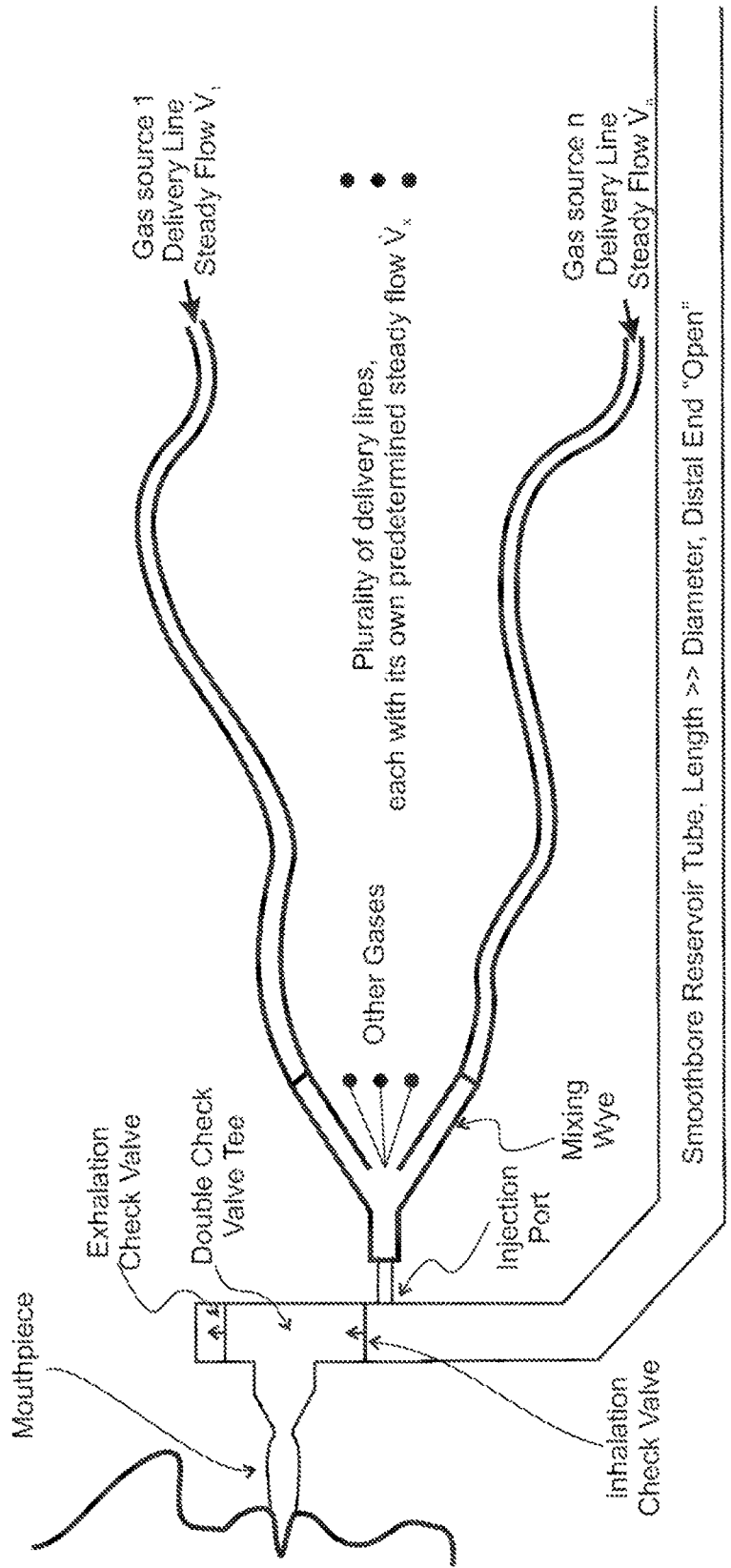
Figure 15:
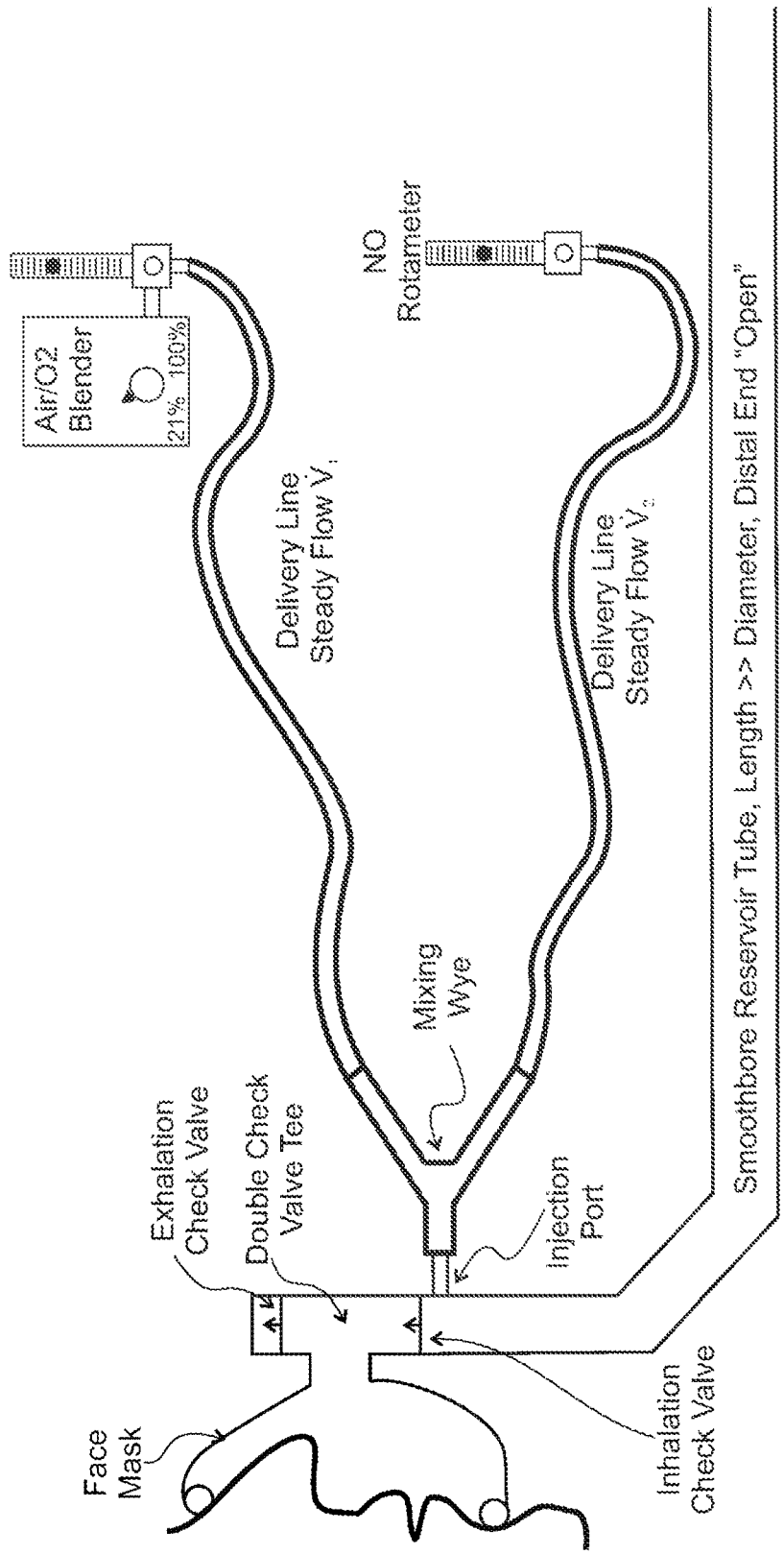
FIG. 15 shows a gas delivery system according to some embodiments of the present invention, where a face mask variant with inhalation and exhalation check valves is fed from a reservoir equipped with an injection port, said injection port supplied with a combined steady flow source of oxygen enriched air and a steady flow source of NO.
Figure 16:
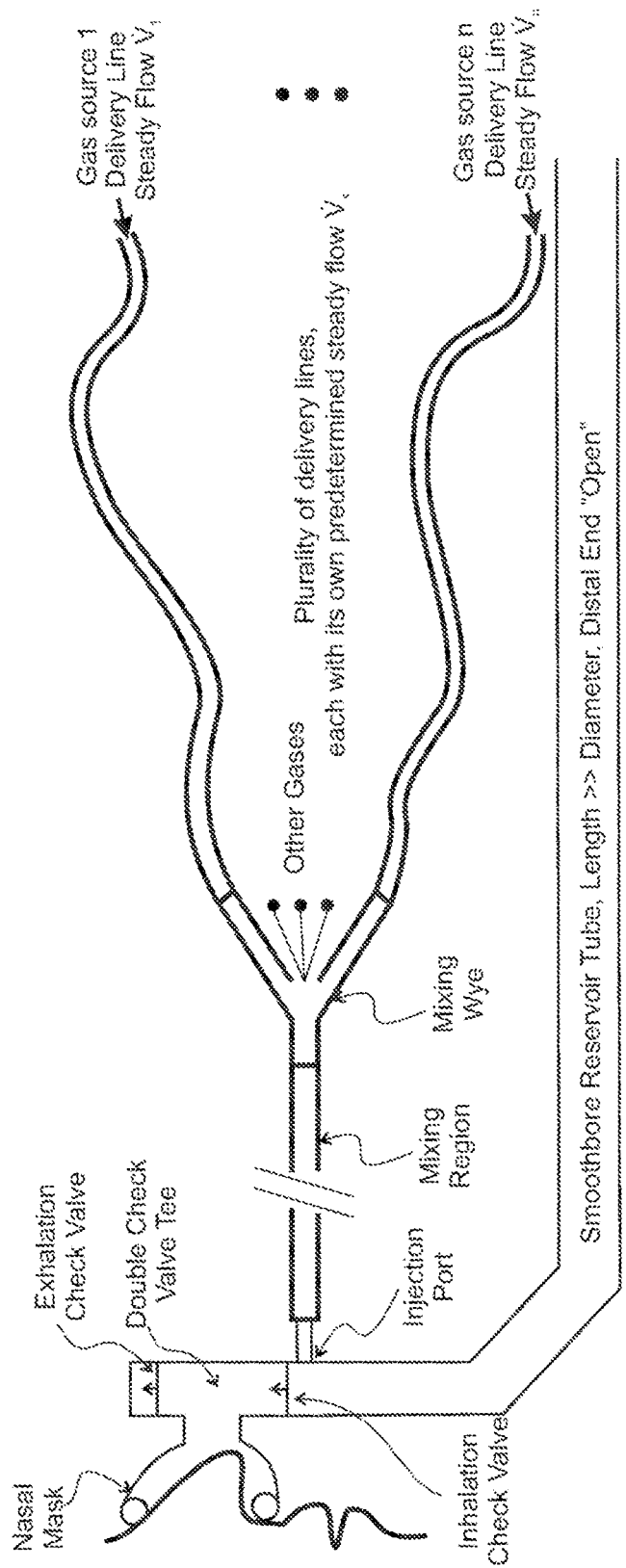
FIG. 16 show gas delivery systems according to some embodiments of the present invention, where one or more therapeutic gases are mixed with one or more diluent gases and these blended gases are merged in a mixing region prior to being injected into the reservoir.
Figure 17:
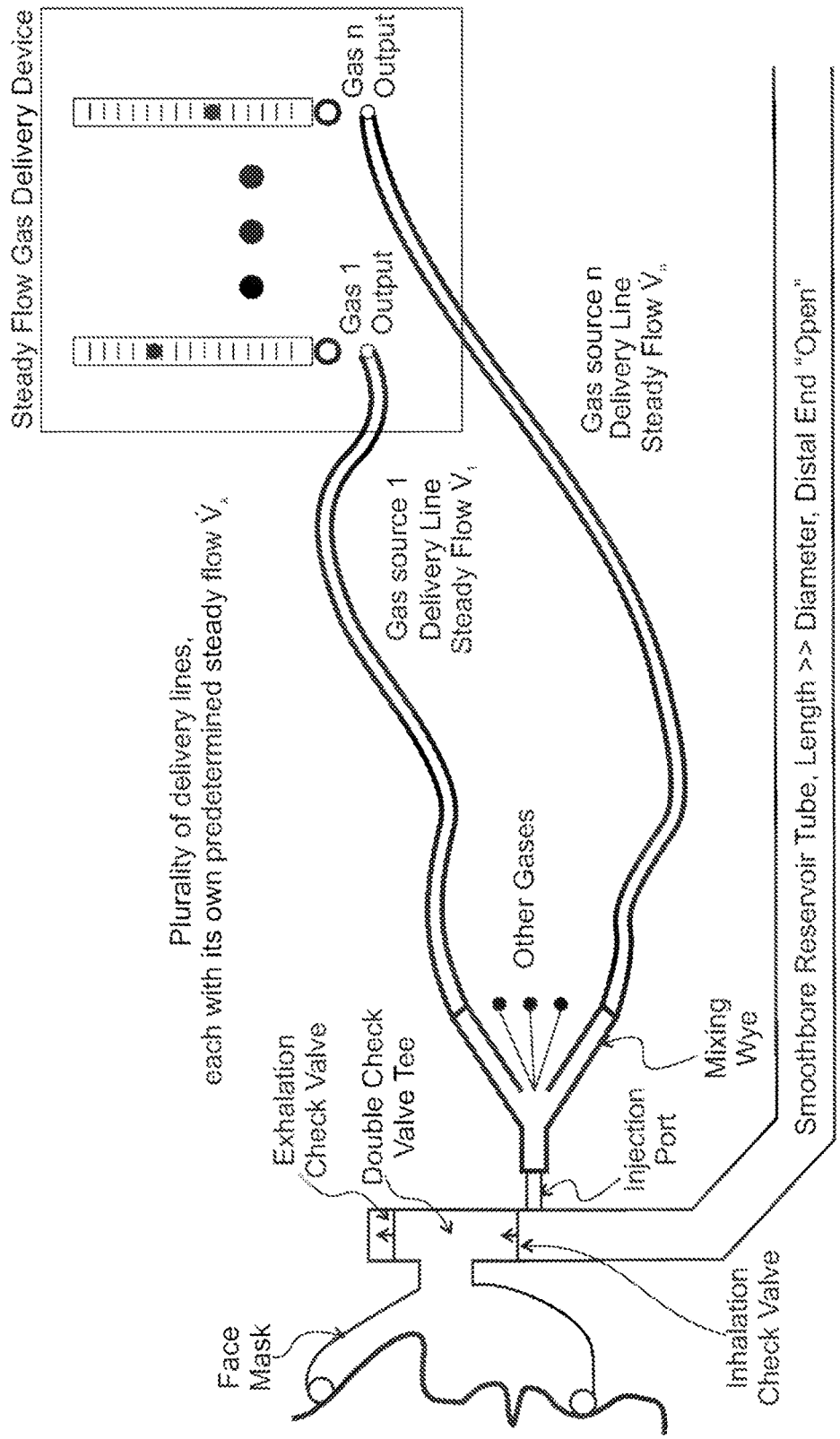
FIG. 17 shows a gas delivery system according to some embodiments of the present invention, where a plurality of incoming gas flows are mixed to create the overall therapeutic gas blend injected into the reservoir, and wherein the individual gas flows are produced by a flow metering system comprising a single unit.

An example of an embodiment of the system of the present invention having a coiled at least one reservoir tube is shown in FIG. 10.

In some embodiments, the flow rate and flow direction in the at least one reservoir tube can be monitored to assess the operation of the reservoir.

Figure 21:
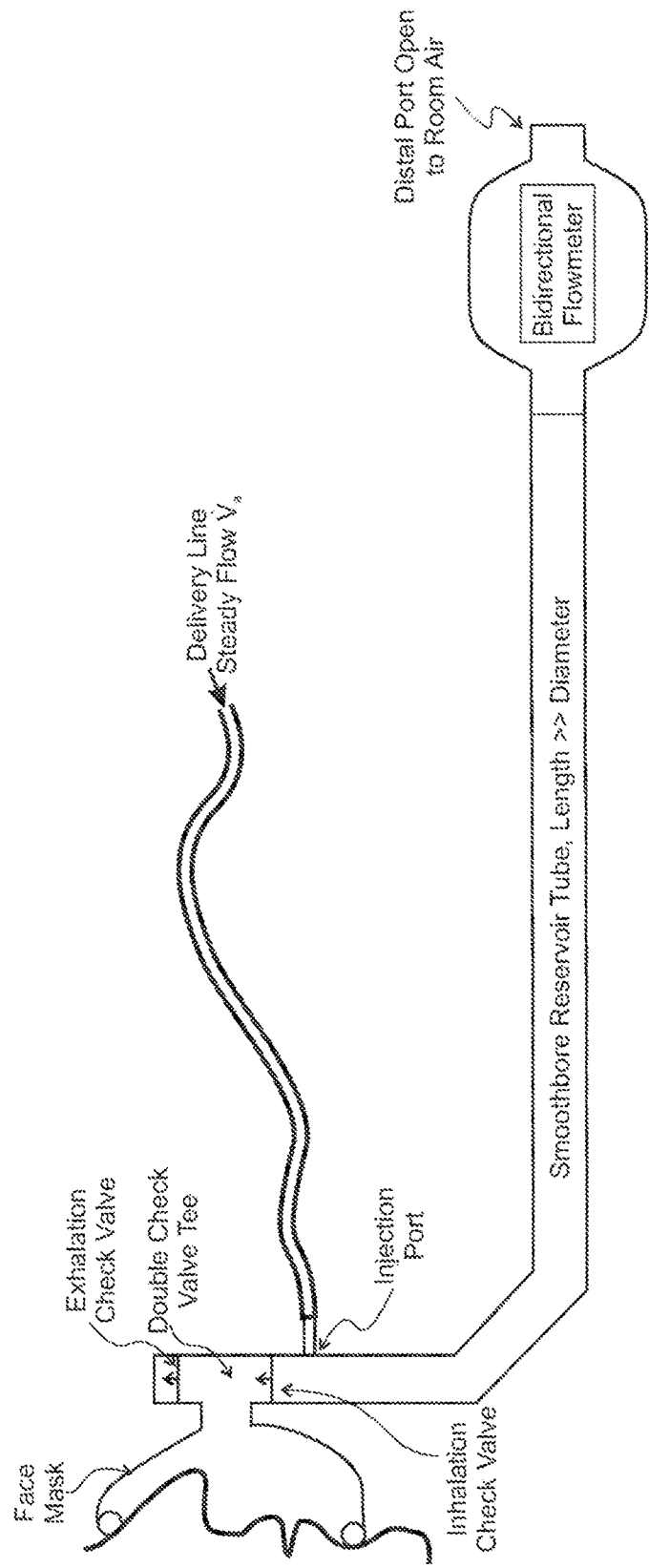
FIG. 21 shows a gas delivery system according to some embodiments of the present invention, where the at least one reservoir tube is further configured to comprise a flow meter at the distal end, and wherein the said flow meter is responsive to both the flow rate and flow direction in the at least one reservoir.

In some embodiments, the at least one reservoir tube further comprises a flow meter at the distal end as shown in, e.g., FIG. 21.

In some embodiments, the system configured to administer at least one therapeutic gas to a patient is further configured to monitor the flow of gas through the proximal end of the at least one reservoir tube by relocating the flowmeter in FIG. 21.

Figure 20:
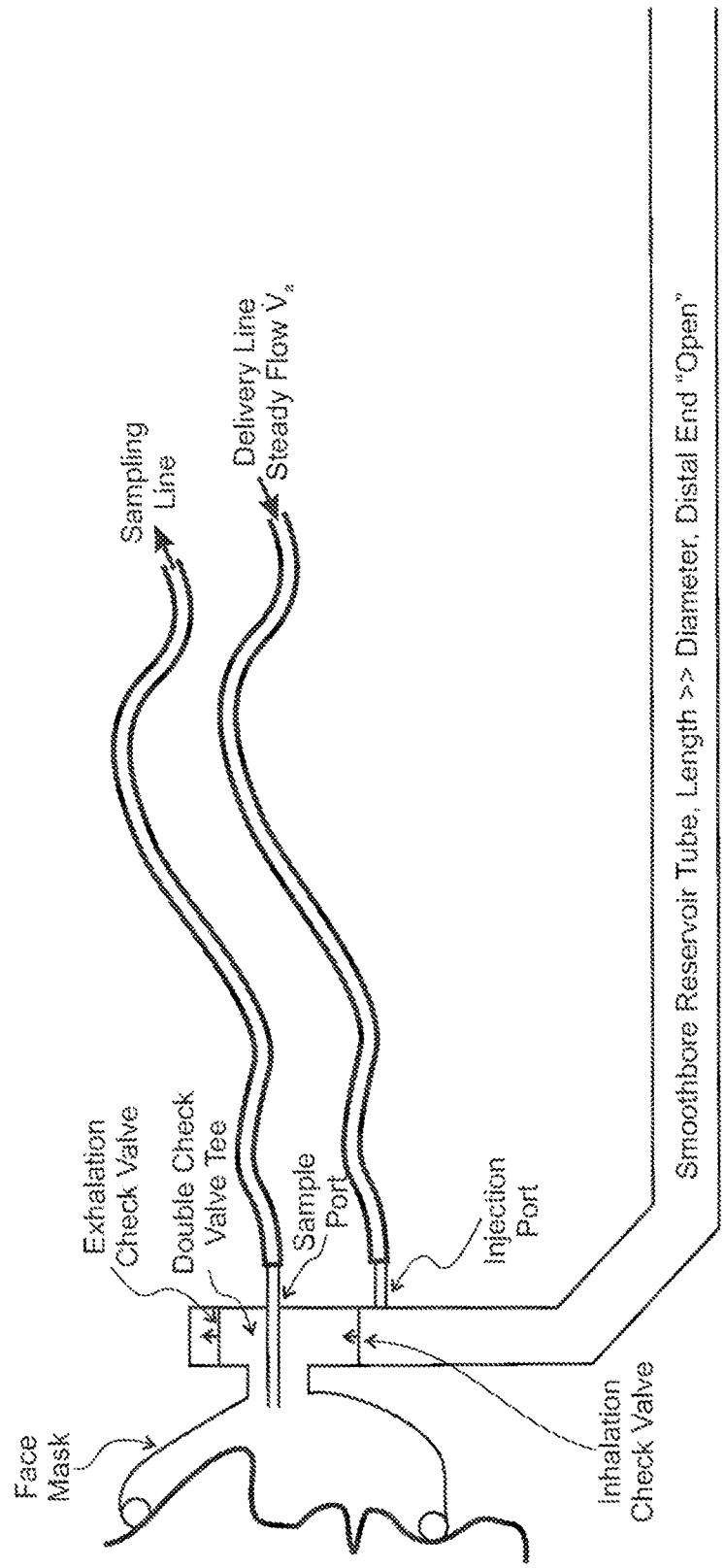
FIG. 20 shows a gas delivery system according to some embodiments of the present invention, wherein the configuration shown in FIG. 5(a) has been modified by adding a sample port between the inhalation and exhalation check valves that provides a means to sample the patient inhaled and exhaled gases.

In some embodiments, the system configured to administer at least one therapeutic gas to a patient is further configured to monitor the at least one therapeutic gas introduced into the system configured to administer at least one therapeutic gas to a patient, as shown in, e.g., FIG. 10 and FIG. 20 via a sampling port and line.

In some embodiments, the at least one reservoir tube further comprises a sampling port at the proximal end.

In some embodiments, the system configured to administer at least one therapeutic gas to a patient is further configured to issue an alert if the monitored value of any one of the concentration the at least one therapeutic gas, or flow rate deviates from a threshold value.

In some embodiments, the system configured to administer at least one therapeutic gas to a patient is further configured to alter the flow rate, and/or the concentration of the at least one therapeutic gas if the monitored value of any one of the concentrations of the constituent gases in the at least one therapeutic gas, or flow rate deviates beyond a threshold value.

Figure 18:
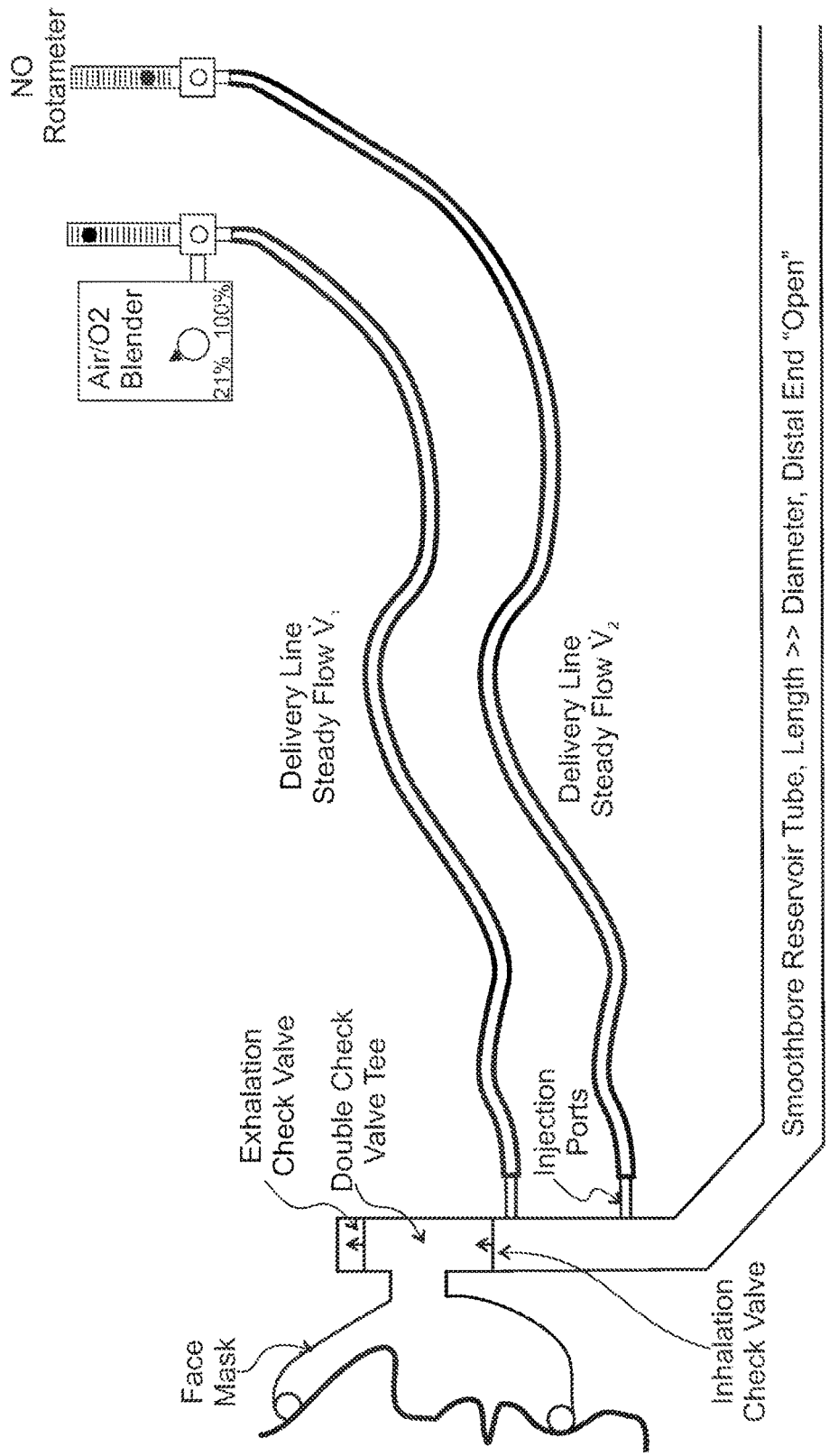
FIG. 18 shows a gas delivery system according to some embodiments of the present invention, where two incoming steady gas flows are mixed to create the overall therapeutic gas blend injected into the reservoir, wherein the first steady gas flow is produced by an enriched oxygen-air blender and the second steady flow is produced by a NO flow metering device.
Figure 19:
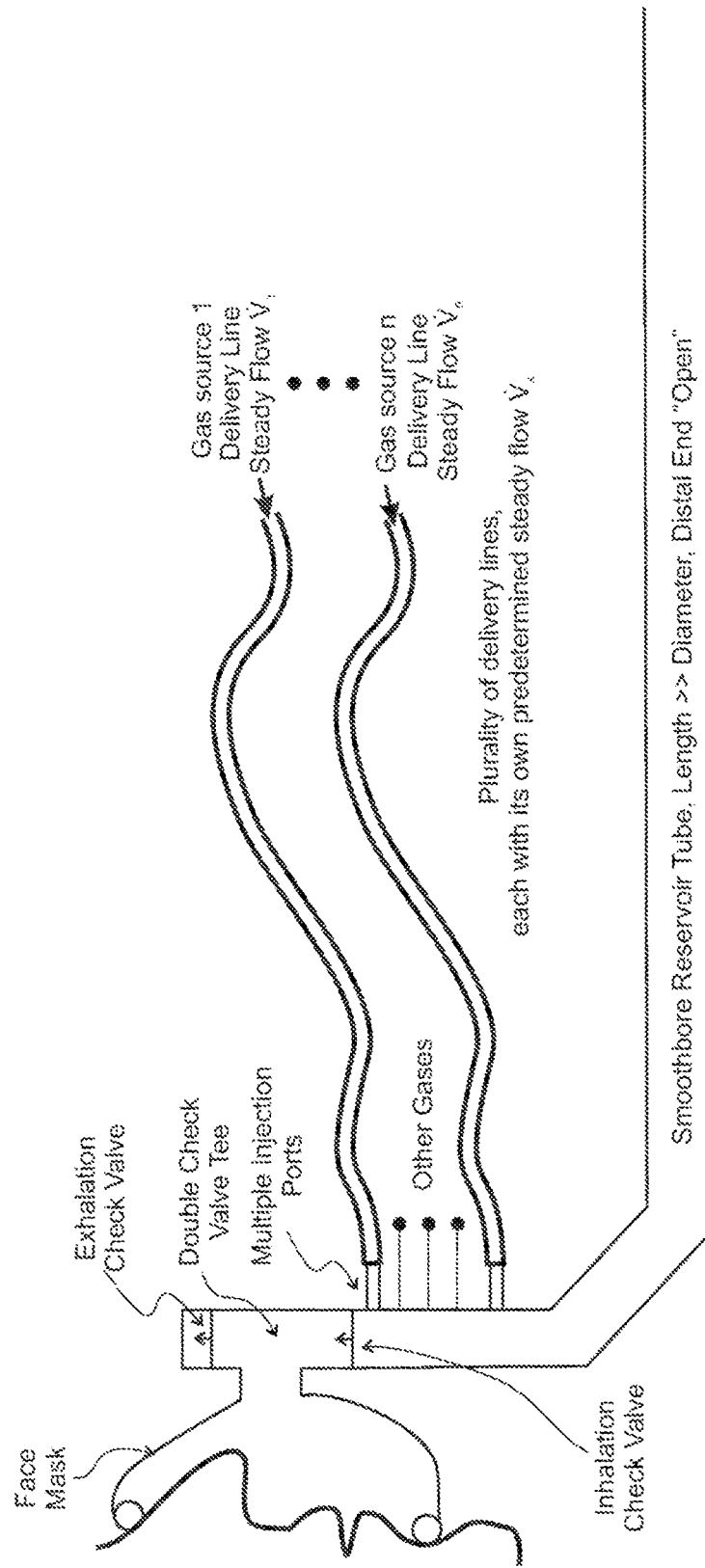
FIG. 19 shows a gas delivery system according to some embodiments of the present invention, where multiple incoming steady gas flows are separately injected into the proximal end of the reservoir.

In some embodiments, the proximal end the at least one reservoir tube has more than one inlet port. On some embodiments a therapeutic gas may be introduced into the system via one inlet port, and a diluent gas may be introduced into the system via a second inlet port. In some embodiments, the therapeutic gas and the diluent gas may be mixed before introduction into the system. FIGS. 11-17 show embodiments wherein the therapeutic gas and the diluent gas are mixed before introduction into the system. FIGS. 18-20 show embodiments wherein the therapeutic gas and the diluent gas are mixed before introduction into the system. FIG. 21 shows an embodiment wherein the at least one reservoir tube is further configured to comprise a flow meter at the distal end.

Figure 22:
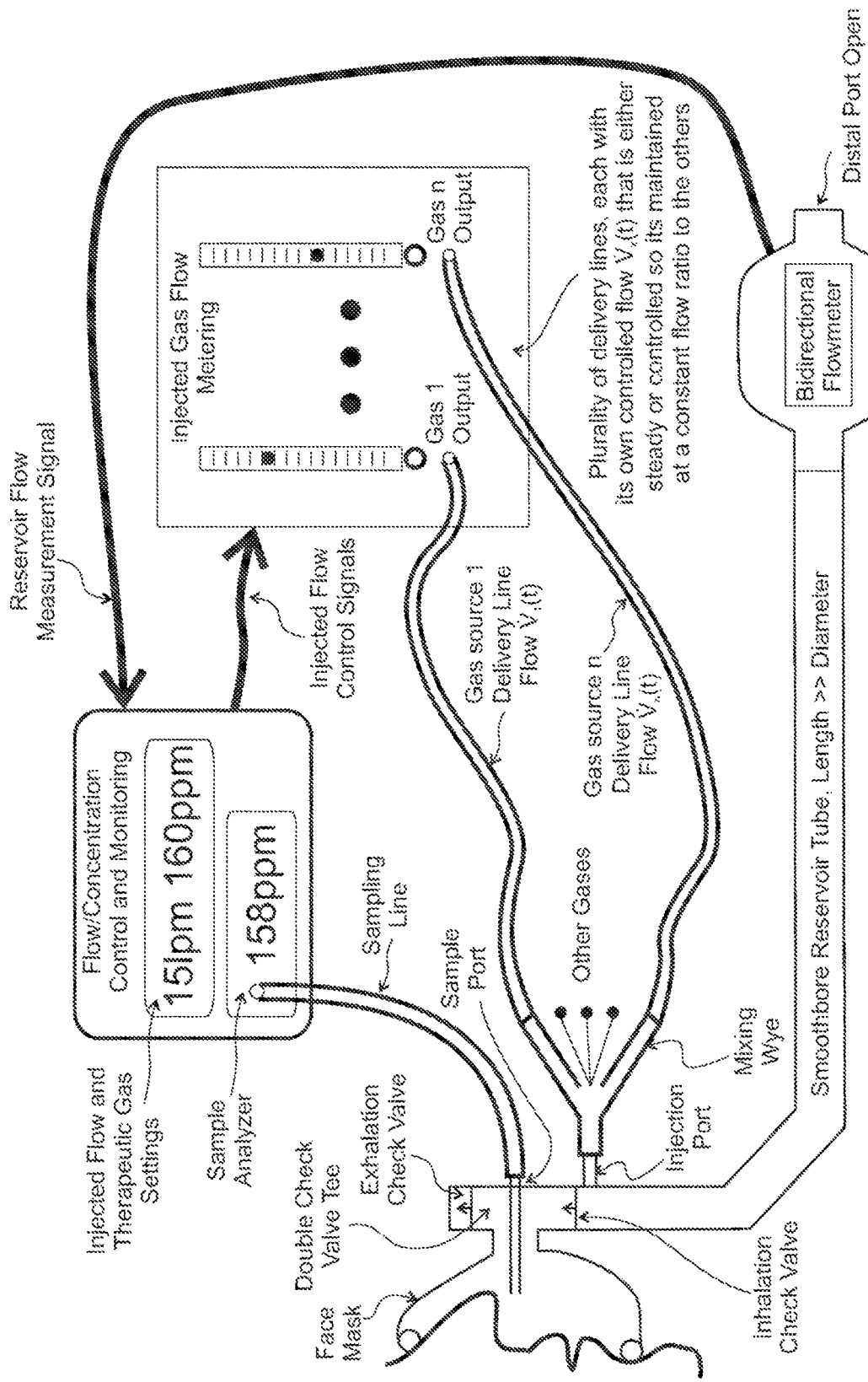
FIG. 22 shows a gas delivery system according to some embodiments of the present invention, where the reservoir is configured to work as part of a therapeutic gas delivery system configured to determine the average injected flow requirement, wherein the average injected flow requirement is determined from the gas flow in the reservoir over a time frame of at least one patient breath period, and wherein the average injected flow rate requirement is used to periodically adjust the average injected flow rate of the at least one therapeutic gas.

FIG. 22 shows a reservoir device as described in some embodiments of the present invention, where the reservoir is configured to work as part of a therapeutic gas delivery system that is capable of:

periodically determining the average injected flow requirement, such periodic determination being based on a flow measurement signal derived from a flowmeter responsive to the average flow and direction of flow in the reservoir, where the flow requirement determination is performed on a time frame longer than one breath but shorter than thirty breaths, and where the total flow of the injected therapeutic gases is periodically adjusted based on the pattern of the recently determined average injected flow requirement, that adjustment carried out simultaneously with maintaining the individual constituent gas flow rates in predetermined fixed ratios, such that the net flow in the reservoir is on average maintained in a generally outgoing direction so that the reservoir is flushed with fresh therapeutic gas on a regular basis. In some embodiments, some embodiments of the system of the present invention are responsive to longer term variations in the patients breathing rhythm without the need to interrupt or adjust flows during an individual breath cycle. In some embodiments, the flow adjustments are performed by a system operator (e.g., but not limited to, an automated device that implements this functionality through analog, digital or computational means as are known to the art). In some embodiments, the system is configured to monitor the reservoir outflow and adjust the total injected therapeutic gas flow by responding to the natural variations in the patient's breathing pattern.

In some embodiments, the at least one reservoir tube is further configured to minimize the effort required by the patient to either inhale, exhale, or both inhale and exhale. In some embodiments, the diameter of the at least one reservoir tube is configured to minimize the effort required by the patient to either inhale, exhale, or both inhale and exhale.

In some embodiments, the at least one reservoir tube is further configured to minimize the effort required by the patient to inhale. In some embodiments, the diameter of the exhaust port and the diameter of the reservoir tube are configured to minimize the effort required by the patient to exhale.

The at Least One Therapeutic Gas

In some embodiments, the at least one therapeutic gas is selected from the group consisting of: oxygen, nitric oxide, carbon monoxide, and nitrous oxide. In some embodiments, the at least one therapeutic gas comprises aerosolized particles, micro particles, nano particles, or any combination thereof, where the aerosolized particles, the micro particles, the nano particles, or any combination thereof are stable in an aerosol suspension for a period consistent with the therapy requirements, typically but not limited to at least 1 day.

In some embodiments, the system of the present invention does not comprise a scrubbing element (e.g., a mechanism configured to remove a portion of the therapeutic gas, e.g., but not limited to, a helium gas, NO, oxygen, etc.).

In some embodiments, the system of the present invention does comprise a scrubbing element (e.g., a mechanism configured to remove a portion of the therapeutic gas, e.g., but not limited to, a diagnostic gas, e.g., a tracer gas).

In some embodiments, the system of the present invention does not comprise a mechanism used to modulate, throttle, gate, or any combination thereof, the flow of therapeutic gas to the patient after the initial flow rates are established.

In some embodiments, the system of the present invention comprises a mechanism used to modulate, throttle, gate, or any combination thereof, the flow of therapeutic gas to the patient after the initial flow rates are established.

In some embodiments, the at least one therapeutic gas is diluted prior to introduction into the system of the present invention. However, in some embodiments, the at least one therapeutic gas is diluted as the gas is introduced into the system of the present invention.

In some embodiments, the gas used to dilute the at least one therapeutic gas contains oxygen. In some embodiments, the gas used to dilute the at least one therapeutic gas contains oxygen and an inert gas, such as nitrogen. In some embodiments, the gas used to dilute the at least one therapeutic gas is compressed air.

In some embodiments, the at least one therapeutic gas is administered along with supplemental oxygen.

In some embodiments, the at least one therapeutic gas and the gas used to dilute the at least one therapeutic gas are stored in compressed gas cylinders. In some embodiments the gases are dispensed using gas flow control apparatus as are known to the art, such as but not limited to rotameters, mass flow meters and positive displacement pumps.

In some embodiments, the therapeutic gas is a mixture of gases, wherein the therapeutic gas is mixed with breathable air.

In some embodiments, the system of the present invention is further configured to reduce the "dead volume" in the patient connection between the patient's airway and the inhalation check valve, thereby reducing the likelihood of the formation of NO2.

In some embodiments, the nitric oxide is stored in and dispensed from cylinders containing medical grade pharmaceutical gas.

In some embodiments, a patient is treated using the system of the present invention, via the methods disclosed in U.S. Patent Application 2015/0044305. In some embodiments, the treatment method further includes monitoring one or more of on-site and off-site parameters such as vital signs, methemoglobin levels, pulmonary function parameters, blood chemistry and hematological parameters, blood coagulation parameters, inflammatory marker levels, liver and kidney function parameters and vascular endothelial activation parameters.

In some embodiments, a patient is treated using the system of the present invention, via the methods disclosed in International Patent Application Publication No. WO 2013132497 A1.

In some embodiments, the at least one reservoir tube further comprises a flow meter at the distal end.

In some embodiments, the at least one reservoir tube further comprises a sampling port at the proximal end.

In some embodiments, the present invention is a system configured to administer at least one therapeutic gas to a patient, comprising:

a. at least one reservoir tube, having a proximal and a distal end, wherein the at least one reservoir tube has a volume within +/−20% of the tidal volume of the patient breath;

b. at least one therapeutic gas inlet at the proximal end of the at least one reservoir tube, wherein a delivery tube is connected to the at least one therapeutic gas inlet and at least one therapeutic gas source; and where the distal end of the reservoir is open to a source of breathable gas at ambient pressure; and c. a patient interface fluidly connected to the proximal end of the at least one reservoir tube via a check valve, wherein the patient interface is configured to form a gas-tight seal between the patient and the system, wherein the inhalation side of a check valve is configured to be closed when the patient is exhaling, wherein the at least one therapeutic gas is introduced into the at least one reservoir tube at the proximal end through the at least one therapeutic gas inlet at a flow rate sufficient to prevent all of the at least one therapeutic gas stored in the at least one reservoir tube from being consumed during a patient's typical single inhalation, and wherein the at least one therapeutic gas flows along the at least one reservoir tube, from the proximal end to the distal end whilst the patient is exhaling, wherein the inhalation side of the check valve is configured to be open when the patient is inhaling, and wherein the inhalation side of the check valve is configured to allow the at least one therapeutic gas to be administered to the patient.

The present invention is further illustrated, but not limited by, the following examples.

EXAMPLES

Example 1: The Effects of the Radius of the Coil of the at Least One Reservoir Tube on Laminar Flow and the Concentration of Nitric Oxide within the at Least One Reservoir Tube An experiment was conducted using 160 ppm nitric oxide was introduced into coiled reservoir tubes having the coil radii shown in the table below. The concentration of nitric oxide within the reservoir tube was compared to the ideal 160 ppm value after the gas had been shuttled back and forth in the reservoir tube simulating a breath cycle.

| $R_{coil}$ (mm) | NO concentration (ppm) | Comments |
|---|---|---|
| 145 | 160 | N/A |
| 120 | 161 | N/A |
| 100 | 162 | At this $R_{coil}$ it was observed that the reservoir tube cross-section turns elliptical. |
| 180 | 162 | N/A |
| 210 | 162 | N/A |

No major changes in NO concentration were observed. It was identified that an approximately 145 mm coil radius could be utilized without causing the reservoir tube to kink or deform noticeably in cross-section. Assuming 145 mm coil radius will be utilized, the critical Reynolds number $Re_{cr}$ will be about 2100. Given this nominal $Re_{cr}$ value, laminar flow should be maintained throughout the breath cycle.

Publications cited throughout this document are hereby incorporated by reference in their entirety.

What is claimed is:

1. A device configured to administer at least one therapeutic gas comprising nitric oxide to a patient, comprising:
   a. at least one reservoir tube, having a proximal and a distal end, wherein the distal end is configured to be open to the ambient environment such that gas moves through the distal end unimpeded and wherein the at least one reservoir tube has a volume larger than a tidal volume of the patient breath;
   b. at least one therapeutic gas inlet at the proximal end of the at least one reservoir tube, wherein a delivery tube is connected to the at least one therapeutic gas inlet and at least one therapeutic gas source; and
   c. a patient interface fluidly connected to the proximal end of the at least one reservoir tube via an inhalation check valve; wherein the patient interface is configured to form a gas-tight seal between the patient and the device; and
   d. a sampling port, wherein the sampling port is distal to the inhalation check valve and proximal to the at least one therapeutic gas inlet.

2. The device of claim 1, further comprising an exhalation check valve.

3. The device of claim 1, wherein the patient interface is selected from a full face mask, a nose mask, a mouthpiece, and a pillow seal nasal cannula.

4. The device of claim 1, wherein the at least one reservoir tube is further configured to minimize the effort required by the patient to inhale.

5. The device of claim 1, further comprising an exhaust port; wherein the diameter of the exhaust port is configured to minimize the effort required by the patient to exhale.

6. The device of claim 1, wherein the device is configured to monitor at least one parameter of the flow of the at least one therapeutic gas through the proximal end of the at least one reservoir tube,
   wherein the at least one parameter comprises: concentration, flow rate, flow volume, contamination, or any combination thereof.

7. The device of claim 1, wherein the at least one reservoir tube further comprises a flow meter at the distal end.

8. The device of claim 1, wherein the sampling port is at the proximal end of the at least one reservoir tube.

9. The device of claim 1, wherein the sampling port is configured to monitor the at least one therapeutic gas delivered to the patient and/or characterize the at least one therapeutic gas delivered to the patient.

10. The device of claim 9, wherein the gas is characterized by content, contamination, flow rate, flow volume, concentration, or any combination thereof.

11. The device of claim 1, wherein the device is further configured to issue an alert if a monitored value of any one of a concentration the at least one therapeutic gas, flow rate, or any combination thereof, deviates from a threshold value.

12. The device of claim 1, wherein the device is further configured to alter the flow rate, a concentration of the at least one therapeutic gas, or any combination thereof.

13. The device of claim 1, wherein the concentration of nitric oxide is 160 ppm in a mixture of oxygen and nitrogen.

14. The device of claim 1, wherein the nitric oxide is at a concentration of 0.5 ppm to 400 ppm.

15. The device of claim 1, further comprising a second check valve, wherein the second check valve is configured to be closed whilst the patient is inhaling, and open whilst the patient is exhaling, and the device is configured to allow the second check valve to vent the gas exhaled by the patient.

\* \* \* \* \*